(12) United States Patent
Harvey

(10) Patent No.: US 8,124,732 B2
(45) Date of Patent: Feb. 28, 2012

(54) COMPOSITION COMPRISING ISOLATED HUMAN CTLA4-FC FUSION PROTEIN PRODUCED IN A TRANSGENIC CHICKEN

(75) Inventor: Alex J. Harvey, Athens, GA (US)

(73) Assignee: Synageva BioPharma Corp., Lexington, MA (US)

(*) Notice: Subject to any disclaimer, the term of this patent is extended or adjusted under 35 U.S.C. 154(b) by 0 days.

(21) Appl. No.: 12/562,899

(22) Filed: Sep. 18, 2009

(65) Prior Publication Data
US 2010/0062982 A1    Mar. 11, 2010

Related U.S. Application Data

(63) Continuation-in-part of application No. 11/973,853, filed on Oct. 10, 2007, now abandoned, which is a continuation-in-part of application No. 11/708,598, filed on Feb. 20, 2007, now Pat. No. 7,511,120, which is a continuation-in-part of application No. 11/370,555, filed on Mar. 8, 2006, now Pat. No. 7,338,654, which is a continuation-in-part of application No. 11/167,052, filed on Jun. 24, 2005.

(60) Provisional application No. 61/217,650, filed on Jun. 2, 2009, provisional application No. 61/192,670, filed on Sep. 19, 2008.

(51) Int. Cl.
*A61K 38/00* (2006.01)
*C07K 16/46* (2006.01)

(52) U.S. Cl. ..................... 530/350; 530/387.1

(58) Field of Classification Search .................. None
See application file for complete search history.

(56) References Cited

U.S. PATENT DOCUMENTS

| | | | |
|---|---|---|---|
| 4,496,537 A | 1/1985 | Kwan | |
| 4,959,317 A | 9/1990 | Sauer | |
| 4,997,763 A | 3/1991 | Hughes et al. | |
| 5,162,215 A | 11/1992 | Bosselman et al. | |
| 5,304,489 A | 4/1994 | Rosen | |
| 5,364,783 A | 11/1994 | Ruley et al. | |
| 5,367,054 A | 11/1994 | Lee | |
| 5,378,618 A | 1/1995 | Sternberg et al. | |
| 5,464,764 A | 11/1995 | Capecchi et al. | |
| 5,487,992 A | 1/1996 | Capecchi et al. | |
| 5,677,177 A | 10/1997 | Wahl et al. | |
| 5,714,353 A | 2/1998 | Pathak et al. | |
| 5,741,957 A | 4/1998 | Deboer et al. | |
| 5,784,992 A | 7/1998 | Petitte et al. | |
| 5,844,095 A | 12/1998 | Linsley et al. | |
| 6,069,133 A | 5/2000 | Chiou et al. | |
| 6,825,396 B2 | 11/2004 | MacArthur | |
| 7,338,654 B2 | 3/2008 | Ivarie et al. | |
| 7,507,873 B2 | 3/2009 | Harvey et al. | |
| 7,524,626 B2 | 4/2009 | Harvey | |
| 7,541,512 B2 | 6/2009 | Rapp et al. | |
| 7,585,963 B2 | 9/2009 | Leavitt et al. | |
| 2002/0108132 A1 | 8/2002 | Rapp | |
| 2002/0182211 A1* | 12/2002 | Peach et al. ........... 424/143.1 |
| 2004/0019923 A1 | 1/2004 | Ivarie et al. | |
| 2007/0092486 A1 | 4/2007 | Yesland | |
| 2007/0243165 A1 | 10/2007 | Ivarie et al. | |
| 2008/0064862 A1 | 3/2008 | Harvey et al. | |
| 2009/0074718 A1 | 3/2009 | Ivarie et al. | |

FOREIGN PATENT DOCUMENTS

| | | |
|---|---|---|
| EP | 0 424 027 A1 | 4/1991 |
| EP | 0 424 044 A1 | 4/1991 |
| WO | WO 90/11355 | 10/1990 |
| WO | WO 94/20608 | 9/1994 |
| WO | WO 95/11302 | 4/1995 |
| WO | WO 97/33998 | 9/1997 |
| WO | WO 97/47739 | 12/1997 |
| WO | WO 98/01027 | 1/1998 |
| WO | WO 03/022040 | 3/2003 |
| WO | WO 03/022228 | 3/2003 |
| WO | WO 2004/047531 | 6/2004 |

OTHER PUBLICATIONS

Harvey et al., Nature Biotech, Apr. 2002, vol. 19, p. 396-399.*
Ivarie, Trends in Biotechnology, Jan. 2003, vol. 21, p. 14-19.*
Lei Zhu et al. 'Production of human monoclonal antibody in eggs of chimeric chickens.' Nature Biotechnology. vol. 23(9), pp. 1159-1169 (2005).
Adolf et al., "Natural human interferon-α2 is O-glycosylated," *Biochem J.*, 276:511-518, (1991).
Allioli et al., "Use of retroviral vectors to introduce and express the β-galactosidase marker gene in cultured chicken primordial germ cells," *Developmental Biology*, 165:30-37 (1994).
Archer et al., "Human growth hormone (hgh) secretion in milk of goats after direct transfer of the hgh gene into the mammary gland by using replication-defective retrovirus vectors," *Proc. Natl. Acad. Sci. USA*, 91:6840-6844 (1994).
Bayley et al., "Exchange of Gene Activity in Transgenic plants catalyzed by the Cre-lox site-specific recombination system," *Plant Molecular Biology*, 18:353-361 (1992).
Beato, M. "Gene regulation by steroid hormones," *Cell*, 56:335-344 (1989).
Bonifer et al., "Tissue specific and position independent expression of the complete gene domain for chicken lysozyme in transgenic mice," *The EMBO Journal*, 9:2843-2848 (1990).
Bosselman et al., "Germline transmission of exogenous genes in the chicken," *Science*, 243:533-535 (1989).
Brazolot et al., "Efficient transfection of chicken cells by lipofection, and introduction of transfected blastodermal cells into the embryo," *Molecular Reproduction and Development*, 30:304-312 (1991).

(Continued)

*Primary Examiner* — Gyan Chandra

(74) *Attorney, Agent, or Firm* — Hak J. Chang; Eugene J. Kim

(57) ABSTRACT

The invention encompasses among other things fusion proteins including Fc fusion proteins such as CTLA4-Fc having avian N-linked glycosylation patterns obtained from egg white of eggs laid by transgenic avians.

6 Claims, 5 Drawing Sheets

OTHER PUBLICATIONS

Briskin et al., "Heritable retroviral transgenes are highly expressed in chickens," *Proc. Natl. Acad. Sci.* USA, 88:1736-1740 (1991).

Brown et al., "Conformational alterations in the proximal portion of the yeast invertase signal peptide do not block secretion," *Mol. Gen. Genet.*, 197:351-357 (1984).

Burns et al., "Vesicular stomatitis virus G glycoprotein pseudotyped retroviral vectors: concentration to very high titer and efficient gene transfer into mammalian and nonmammalian cells," *Proc. Natl. Acad. Sci.* USA, 90:8033-8037 (1993).

Chung et al., "A 5' element of the chicken β-globin domain serves as an insulator in human erythroid cells and protects against position effect in drosophila," *Cell*, 74:505-514 (1993).

Cosset et al., "Improvement of avian leucosis virus (ALV)-based retrovirus vectors by using different cisacting sequences from ALVs," *Journal of Virology*, 65:3388-3394 (1991).

Cosset et al., "Use of helper cells with two host ranges to generate high-titer retroviral vectors," *Virology* 193:385-395 (1993).

Dean et al., "Regulation of the chicken *ovalbumin* gene by estrogen and corticosterone requires a novel DNA element that binds a labile protein, chirp-1," *Molecular and Cellular Biology*, 16:2015-2024 (1996).

Deeley et al., "Synthesis and Deposition of Egg Proteins," eds Robert J. Etches, Ph.D, D.Sc.and Ann M. Verrinder Gibbins, Ph.D., Manipulation of the Avian Genome, Boca Raton, CRC Press (1993), p. 205.

Dierich et al., "Cell-specificity of the chicken *ovalbumin* and *conalbumin* promoters," *The EMBO Journal*, 6:2305-2312 (1987).

Dugaiczyk et al., "The *ovalbumin* gene: cloning and molecular organization of the entire natural gene," *Proc. Natl. Acad. Sci.* USA, (1979).

Etches et al., "Contributions to somatic and germline lineages of chicken blastodermal cells maintained in culture," *Molecular Reproduction and Development*, 45:291-298 (1996).

Fiering S. et al., "An "in-out" strategy using gene targeting and FLP recombinase for the functional dissection of complex DNA regulatory elements: Analysis of the β-globin locus control region," *Proc. Natl. Acad. Sci* USA, vol. 90, 18, Sep. 15, 1993, pp. 8469-8473.

Fisher et al., "Expression of exogenous protein and analysis of morphogenesis in the developing chicken heart using an adenoviral vector," *Cardiovascular Research*, 31:E86-E95 (1996).

Galton et al., "Antibodies to Lymphoblastoid Interferon," *Lancet*, 2:572-573, (1989).

Gannon et al., "Organization and sequences at the 5' end of a cloned complete *ovalbumin* gene," *Nature*, 276:428-434 (1979).

Gilbert, Egg albumin and its formation in Physiology and Biochemistry of the Domestic Fowl, Bell and Freeman, eds., Academic Press, London, NY, pp. 1291-1329, (1971).

Gu et al., "Deletion of a DNA polymerase β gene segment in T cells using cell type-specific gene targeting," *Science*, 265:103-106 (1994).

Haecker et al., "Repression of the *ovalbumin* gene involves multiple negative elements including an ubiquitous transcriptional silencer," *Molecular Endocrinology*, 9:1113-1126 (1995).

Hale, K.L., "Oncolog, Interferon: The Evolution of a Biological Therapy, Taking a New Look at Cytokine Biology," *M.D. Anderson Oncolog*, 39(4):1-4 (1994).

Hogan et al., "Manipulating the Mouse Embryo," Cold Spring Harbor Laboratory, NY, (1988).

Johnson et al., "pXeX, a vector for efficient expression of cloned sequences in *Zenopus* embryos," *Gene*, 147:223-226 (1994).

Kato et al., "A far upstream estrogen response element of the *ovalbumin* gene contains several half-palindromic 5'-TGACC-3' motifs acting synergistically," *Cell*, 68:731-742 (1992).

Kaye et al., "A close association between sites of Dnase I hypersensitivity and sites of enhanced cleavage by micrococcal nuclease in the 5'-flanking region of the actively transcribed *ovalbumin* gene," *The EMBO Journal*, 3:1127-1144 (1984).

Kotani et al., "Improved methods of retroviral vector transduction and production for gene therapy," *Hum. Gene Ther.* 5:19-28 (1994).

Lai et al., "The *ovalbumin* gene: structural sequences in native chicken DNA are not contiguous," *Proc. Natl. Acad. Sci.* USA, 75:2205-2209 (1978).

Lin et al., "Integration and germ-line transmission of a pseudotyped retroviral vector in zebrafish," *Science*, 265:666-669 (1994).

Lobe et al., "Conditional genome alteration in mice," *BioEssays*, 20:200-208 (1998).

Logie et al., "Ligand-regulated site-specific recombination," *Proc. Natl. Acad. Sci.* USA, 92:5940-5944 (1995).

Lou et al., "Adenovirus-mediated gene transfer into tendon and tendon sheath," *Journal of Orthopaedic Research*, 14:513-517 (1996).

Lobe et al., "Transgenic birds by DNA microinjection," *Bio/Technology*, 12:60-63 (1994).

Moore et al., "The development of β-lactamase as a highly versatile genetic reporter for eukaryotic cells," *Analytical Biochemistry*, 247:203-209 (1997).

Mountford et al., "Dicistronic targeting constructs: reporters and modifiers of *mammalian* gene expression," *Proc. Natl. Acad. Sci.* USA, 91:4303-4307 (1994).

Muramatsu, T. et al., "Gene gun-mediated in vivo analysis of tissue-specific repression of gene transcription driven by the chicken *ovalbumin* promoter in the liver and oviduct of laying hens." *Molecular and Cellular Biochemistry*, vol. 185, No. 1-2, Aug. 1998, pp. 27-32.

Myllya et al., *Biochem J.*, 196:683-692 (1981).

Nordstrom et al., "A complex array of double-stranded and single-stranded DNA-binding proteins mediates induction of the *ovalbumin* gene by steroid hormones," *The Journal of Biological Chemistry*, 268:13193-13202 (1993).

Nyman et al., Structural characterisation of N-linked and O-lined oligosaccharides derived from interferon-α2b and interferon-α14c produced by Sendai-virus-induced human peripheral blood leukocutes, *Eur. J. Biochem.*, 253:485-493 (1998).

Ochiai et al., Synthesis of human erythropoietin in vivo in the oviduct of laying hens by localized in vivo gene transfer using electroporation, *Poultry Science*, 77:299-302 (1998).

Odell et al., "Seed-specific gene activation mediated by the cre/lox site-specific recombination system," *Plant Physiol.*, 106:447-458 (1994).

Often et al., "The MMTV LTR promoter is induced by progesterone and dihydrostestosterone but not by estrogen," *Molecular Endocrinology*, 2:143-147 (1988).

Palmiter, R.D., "Quantitation of parameters that determine the rate of *ovalbumin* synthesis," *Cell*, 4:189-197 (1975).

Palmiter, R.D., "Rate of ovalbumin messenger ribonucleic acid synthesis in the oviduct of estrogen-primed chicks," *The Journal of Biological Chemistry*, 248:8260-8270 (1973).

Park et al., "Modulation of transcriptional activity of the chicken *ovalbumin* gene promoter in primary cultures of chicken oviduct cells: effects of putative regulatory elements in the 5'-flanking region," *Biochemistry and Molecular Biology International*, 36:811-816 (1995).

Roop et al., "Definition of the 5' and 3' ends of transcripts of the *ovalbumin* gene," *Cell*, 19:63-68 (1980).

Royal et al., "The *ovalbumin* gene region: common features in the organization of three genes expressed in chicken oviduct under hormonal control," *Nature*, 279:324-331 (1997).

Rucker et al., "Cre-mediated recombination at the murine whey acidic protein (mWAP) locus," *Molecular Reproduction and Development*, 48:324-331 (1997).

Sanders et al., "Positive and negative regulatory elements control the steroid-responsive *ovalbumin* promoter," *Biochemistry*, 27:6550-6557 (1988).

Sang TIBTECH 12:415-420 (1994).

Sauer, B., "Manipulation of transgenes by site-specific recombination: use of cre recombinase," *Methods in Enzymology*, 225:890-900 (1993).

Schweers et al., "A protein with a binding specificity similar to NF-$_k$B binds to a steroid-dependent regulatory element in the *ovalbumin* gene," *The Journal of Biological Chemistry*, 266:10490-10497 (1991).

Simkiss, "Transgenic birds, animals with novel genes," McLean ed., Cambridge Univ. Press NY pp. 106-135 (1994).

Thoraval et al., "Germline transmission of *exogenous* genes in chickens using helper-free ecotropic avian leucosis virus-based vectors," *Transgenic Research*, 4:369-376 (1995).

Uyeda et al., "Cloning and sequencing of hen magnum cDNAs encoding viteline membrane outer layer protein I (VMO-1)," *Gene*, 144:311-312 (1994).

Vick et al., "Transgenic birds from transformed primordial germ cells," *Proc. R. Soc. Lond. B.*, 179-183 (1993).

Wentworth et al., "Manipulation of Avian Primordial Germ Cells and Gonadal Differentiation," *Poultry Science*, 68(7):999-1010 (1988).

Yee et al., "Generation of high-titer pseudotyped retroviral vectors with very broad host range," *Methods in Cell Biology*, 43:99-112 (1994).

Zhang et al., "Inducible site-directed recombination in mouse embryonic stem cells," *Nucleic Acids Research*, 24:543-548 (1996).

Zolotukhin et al., "A "humanized" green fluorescent protein cDNA adapted for high-level expression in mammalian cells," *Journal of Virology*, 70:4646-4654 (1996).

Rendell, et al., Bichem. And Mol. Biol. 81:819-822, (1985).

Rohrer, J.s. and White, H.B., Biochem J. 285:275-280, 1992.

Anderson et al., Monosaccharide and oligosaccharide analysis of isoelectric focusing-separated and blotted granulocyte colony-stimulating factor glycoforms using high-pH anion-exchange chromatography with pulsed amperometric detection, Glycobiology, 4:(4)459-467 (1994).

Carter et al., The significance of carbohydrates on G-CSF: differential sensitivity of G-CSFs to human neutrophil elastase degradation, Journal of Leukocyte Biology, 75:515-522 (2004).

Dipaola et al., Interferon-A2 Produced by Normal Human Leukocytes Is Predominantly Interferon-A2b, Journal of Interferon Research, 14:325-332 (1994).

Gewert et al., Analysis of Interferon-A2 Sequences in Human Genomic DNA, Journal of Interferon Research, 13:227-231 (1993).

Holloway, Applications of Recombinant DNA Technology in the Production of Glycosylated Recombinant Human Granulocyte Colony Stimulating Factor, European Journal of Cancer, 30A:(Suppl 3)S2-S6 (1994).

Nomura et al., Purification and characterization of human granulocyte colony-stimulating factor (G-CSF), The EMBO Journal, 5:(5) 871-876 (1986).

Oheda et al., Structures of Sugar Chains of Recombinant Human Granulocyte-Colony-Stimulating Factor Produced by Chinese Hamster Ovary Cells, Journal of Biochemistry, 103:544-546 (1998).

Fukuda et al, Survival of Recombinant Erythropoietin in the Cirrculation: The Role of Carbohydrates, Blood, vol. 73, No. 1, 84-89 (1989).

Higuchi et al, Role of Sugar Chains in the Expression of the Biological Activity of Human Erythropoietin*, The Journal of Biological Chemistry, vol. 287, No. 11, 7703-7709 (1992).

Mirimoto et al, Biological and physicochemical characterization of recombinant human erythropoietins fractionated by Mono Q column chromatography and their modification with sialyltransferase, Glycoconjugate Journal, 13:1013-1020 (1996).

Sasaki et al, Carbohydrate Structure of Erythropoietin Expressed in Chinese Hamster Ovary Cells by a Human Erythropoietin cDNA*, The Journal of Biological Chemistry, vol. 262, No. 25, 12059-12076 (1987).

Skibeli et al, Sugar profiling proves that human serum erythropoietin differs from recombinant human erythropoietin, Blood, vol. 98, No. 13, 3626-3634 (2001).

Storring et al, Epoetin alfa and beta differ in their erythropoietin isoform compositions and biological properties, British Journal of Haematology, 100:79-89 (1998).

Takeuchi et al, Comparative Study of the Asparagine-linked Sugar Chains of Human Erythropoietins Purified from Urine and the Culture Medium of Recombinant Chinese Hamster Ovary Cells*, The Journal of Biological Chemistry, vol. 283, No. 8, 3657-3663 (1988).

Takeuchi et al, Relationship between sugar chain structure and biological activity of recombinant human erythropoietin produced in Chinese hamster ovary cells, Proc. Natl. Acad, Sci. USA, vol. 86, 7819-7822 (1989).

Takeuchi et al, Role of Sugar Chains in the in Vitro Biological Activity of Human Erythropoietin Produced in Recombinant Chinese Hamster Ovary Cells*, The Journal of Biological Chemistry, vol. 265, No. 21, 12127-12130 (1990).

Wasley et al, The Importance of N- and O-Linked Oligosaccharides for the Biosynthesis and In Vitro and In Vivo Biologic Activities of Erythropoietin, Blood, vol. 77, No. 12, 2624-2632 (1991).

Coll et al, Stimulation of Heme Accumulation and Erythroid Colony Formation in Cultures of Chick Bone Marrow Cells by Chicken Plasma, J. Cell Biol. 76: 184-190 (1978).

Elliott et al, Secretion of Glycosylated Human Erythropoietin from Yeast Directed by the α-Factor leader Region, Gene, 79: 167-180 (1989).

Lee et al, *Heterologous* Gene Expression in Avian Cells: Potential as a Producer of Recombinant Proteins, Biomed Sci. 6: 8-17 (1999).

Li et al, Glycosylated and Phosphorylated Proteins—Expression in Yeast and Oocytes of Xenopus: Prospects and Challenges—Relevance to Expression of Thermostable Proteins, Prot Expr. And Purif. 22: 369-380 (2001).

Ochiai et al, Synthesis of Human Erythropoietin In Vivo in the Oviduct of Laying Hens by Localized In Vivo Gene Transfer Using Electroporation, Poultry Sci. 77: 299-302 (1989).

Stamper, et al., Crystal structure of the B&-1/CTLA-4 complex that inhibits human immune responses, Nature, vol. 410, 608-611 (2001).

Linsley, et al., CTLA-4 Is a Second Receptor for the B Cell Activation Antigen B7, J. Exp. Med., vol. 174, 561-569 (1991).

Weiner, et al. A sensitive enzyme immunocassay for the quantitation of human CTLA4Ig fusion protein in mouse serum: pharmacokinetic qpplication to optimizing cell line selection, Elsevier Sciences B.V., 15:571-579, (1997).

Srinivas, et al., Pharmacokinetics and Pharmacodynamics of CTLA4Ig (BMS-188667), a Novel Immunosuppressive Agent, in Monkeys following Multiple Doses, Journal of Pharmaceutical Sciences, vol. 85, No. 1, 1-4 (1996).

Srinivas, et al., Assessment of Dose Proportionality, Absolute Bioavailability, and Immunogenicity Response of CTLA4Ig (BMS-188667), a novel Immunosuppressive Agent, Following Subcutaneous and Intravenous Administration to Rats, Pharmaceutical Research, vol. 14, No. 7, 911-916 (1997).

Kim, et al., The Glycosylation and Pharmacokinetics of CTLA4Ig Produced in Rice Cells, Biol. Pharm. Bull. 30(10) 1913-1917 (2007).

Lui, et al., Mammary gland-specific secretion of biologically active immunosuppressive agent cytotoxic-T-lymphocyte antigen 4 human immunoglobulin fusion protein (CTLA4Ig) in milk by transgenesis, Journal of Immunological Methods, 277, 171-183 (2003).

Alegre, et al., T-Cell Regulation by CD28 and CTLA-4, Macmillian Magazines Ltd., vol. 1, 220-228 (2001).

Moreland, et al., Costimulatory blockade in patients with rheumatoid arthritis: a pilot, dose-finding, double-blind, placebo-controlled clinical trial evaluating CTLA-4Ig and LEA29Y eighty-five days after the first infusion, Arthritis Rheum., 46(6):1470-9 (2002).

Bristol-Myers Squibb Company (News Release), Data Show Bristol-Myers Squibb's BMS-188667 (CTLA4Ig), An Investigational Costimulation Blocker, Provided Improvement in Rheumatoid Arthritis Activity When Added to Methotrexate therapy, Oct. 26, 2002.

Bluestone, J. A., CTLA-4Ig is Finally Making It: A personal Perspective, American Journal of Transplantation, 5, 423-424 (2005).

Ruderman, and Pope, The evolving clinical profile of abatacept (CTLA4-Ig): a novel co-stimulatory modulator for the treatment of rheumatoid arthritis, Arthritis Research & Therapy, vol. 7, Suppl 2, (2005).

Harper, et al., CTLA-4 and CD28 Activated Lymphocyte Molecules are Closely Related in Both Mouse and Human as to Sequence, Message Expression, Gene Structure, and Chromosomal Location, The Journal of Immunology, vol. 147, No. 3, 1037-1044 (1991).

Dariavach, et al., Human Ig superfamily CTLA-4 gene: chromosomal localization and identity of protein sequence between murine and human CTLA-4 cytoplasmic domains, Eur. J. Immunol. 18: 1901-1905 (1988).

Adams, et al., Calcineurin Inhibitor—Free CD28 Blockade-Based Protocol Protects Allogeneic Islets in Nonhuman Primates, Diabetes, vol. 51, 265-270.

NCBI Accession NM_005214. *Homo sapiens* cytotoxic T-lymphocyte-associated protein 4 (CTLA4) [gi:21361211], (2006).

Anderson, et al., Cloning and Expression of cDNA Encoding Human Lsosomal acid lipase/cholesteryl ester hydrolase. Similarities to gastric and lingual lipases, J. Biol. Chem.., 266: 22479-22484 (1991).

Lee, et al., Generation and Characterization of a novel single-gene-encoded single-chain immunoglobulin molecule with antigen binding activity and effector functions, Molecular Immunology 36, 61-71 (1999).

Sando, et al., Human Lysosomal acid lipase/cholesteryl ester hydrolase. Purification and properties of the form secreted by fibroblasts in microcarrier culture, J. Biol.Chem, 260:15186-15193 (1985).

Sorge, et al, Molecular Cloning and Nucleotide Sequence of Human Glucocerebrosidase cDNA, Proc. Natl. Acad. Sci, vol. 82. 7289-7293 (1985).

* cited by examiner

DQEPKSSDKTHTSPPSPAPELLGGSSVFLFPPKPKDTLMIS
RTPEVTCVVVDVSHEDPEVKFNWYVDGVEVHNAKTKPRE
EQYNSTYRVVSVLTVLHQDWLNGKEYKCKVSNKALPAPIE
KTISKAKGQPREPQVYTLPPSRDELTKNQVSLTCLVKGFY
PSDIAVEWESNGQPENNYKTTPPVLDSDGSFFLYSKLTVD
KSRWQQGNVFSCSVMHEALHNHYTQKSLSLSPGK

FIG. 1

MGVLLTQRTLLSLVLALLFPSMASMAMHVAQPAVVLASSR
GIASFVCEYASPGKATEVRVTVLRQADSQVTEVCAATYMM
GNELTFLDDSICTGTSSGNQVNLTIQGLRAMDTGLYICKVE
LMYPPPYYLGIGNGTQIYVIDPEPCPDSDQEPKSSDKTHTS
PPSPAPELLGGSSVFLFPPKPKDTLMISRTPEVTCVVVDVS
HEDPEVKFNWYVDGVEVHNAKTKPREEQYNSTYRVVSVL
TVLHQDWLNGKEYKCKVSNKALPAPIEKTISKAKGQPREP
QVYTLPPSRDELTKNQVSLTCLVKGFYPSDIAVEWESNGQ
PENNYKTTPPVLDSDGSFFLYSKLTVDKSRWQQGNVFSC
SVMHEALHNHYTQKSLSLSPGK

FIG. 2 sggkltavdpetnmnvseiisywgfpseeylvetedgyilclnriphgrknhsdkgpkpvvflqhglladssnwvt
nlansslgfiladagfdvwmgnsrgntwsrkhktlsvsqdefwafsydemakydlpasinfilnktgqeqvyyvg
hsqgttigfiafsqipelakrikmffalgpvasvafctspmaklgrlpdhlikdlfgdkeflpqsaflkwlgthvcthvilk
elcgnlcfllcgfnernlnmsrvdvytthspagtsvqnmlhwsqavkfqkfqafdwgssaknyfhynqsyppty
nvkdmlvptavwsgghdwladvydvnilltqitnlvfhesipewehldfiwgldapwrlynkiinlmrkyq

FIG. 5A arpcipksfgyssvvcvcnatycdsfdpptfpalgtfsryestrsgrrmelsmgpiqanhtgtgllltlqpeqkfqkv
kgfggamtdaaalnilalsppaqnlllksyfseegigyniirvpmascdfsirtytyadtpddfqlhnfslpeedtklki
plihralqlaqrpvsllaspwtsptwlktngavngkgslkgqpgdiyhqtwaryfvkfldayaehklqfwavtaen
epsagllsgypfqclgftpehqrdfiardlgptlansthhnvrllmlddqrlllphwakvvltdpeaakyvhgiavhw
yldflapakatlgethrlfpntmlfaseacvgskfweqsvrlgswdrgmqyshsiitnllyhvvgwtdwnlalnpeg
gpnwvrnfvdspiivditkdtfykqpmfyhlghfskfipegsqrvglvasqkndldavalmhpdgsavvvvlnrs
skdvpltikdpavgfletispgysihtylwrrq

FIG. 5B

SEQUENCE LISTING

```
<160> NUMBER OF SEQ ID NOS: 14

<210> SEQ ID NO 1
<211> LENGTH: 234
<212> TYPE: PRT
<213> ORGANISM: Artificial Sequence
<220> FEATURE:
<223> OTHER INFORMATION: IgG1 Fc Fragment

<400> SEQUENCE: 1

Asp Gln Glu Pro Lys Ser Ser Asp Lys Thr His Thr Ser Pro Pro Ser
1               5                   10                  15

Pro Ala Pro Glu Leu Leu Gly Gly Ser Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
        115                 120                 125

Gln Pro Arg Glu Pro Gln Val Tyr Thr Leu Pro Pro Ser Arg Asp Glu
    130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190

Leu Tyr Ser Lys Leu Thr Val Asp Lys Ser Arg Trp Gln Gln Gly Asn
        195                 200                 205

Val Phe Ser Cys Ser Val Met His Glu Ala Leu His Asn His Tyr Thr
    210                 215                 220

Gln Lys Ser Leu Ser Leu Ser Pro Gly Lys
225                 230

<210> SEQ ID NO 2
<211> LENGTH: 383
<212> TYPE: PRT
<213> ORGANISM: Artificial Sequence
<220> FEATURE:
<223> OTHER INFORMATION: CTLA4-Fc

<400> SEQUENCE: 2

Met Gly Val Leu Leu Thr Gln Arg Thr Leu Leu Ser Leu Val Leu Ala
```

|   1   |       |   5   |       |       |       |  10   |       |       |       |  15   |       |
|-------|-------|-------|-------|-------|-------|-------|-------|-------|-------|-------|-------|
| Leu   | Leu   | Phe   | Pro   | Ser   | Met   | Ala   | Ser   | Met   | Ala   | Met   | His   | Val | Ala | Gln | Pro |

Leu Leu Phe Pro Ser Met Ala Ser Met Ala Met His Val Ala Gln Pro
                    20                  25                  30

Ala Val Val Leu Ala Ser Ser Arg Gly Ile Ala Ser Phe Val Cys Glu
                35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
                100                 105                 110

Thr Gly Leu Tyr Ile Cys Lys Val Glu Leu Met Tyr Pro Pro Pro Tyr
            115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
                180                 185                 190

Pro Glu Val Thr Cys Val Val Val Asp Val Ser His Glu Asp Pro Glu
            195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
                260                 265                 270

Ser Lys Ala Lys Gly Gln Pro Arg Glu Pro Gln Val Tyr Thr Leu Pro
            275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
                340                 345                 350

Trp Gln Gln Gly Asn Val Phe Ser Cys Ser Val Met His Glu Ala Leu
            355                 360                 365

His Asn His Tyr Thr Gln Lys Ser Leu Ser Leu Ser Pro Gly Lys
    370                 375                 380

<210> SEQ ID NO 3
<211> LENGTH: 11868
<212> TYPE: DNA
<213> ORGANISM: Artificial Sequence
<220> FEATURE:
<223> OTHER INFORMATION: pSIN-OV-3.5-I-CTLA4-inv Vector

<400> SEQUENCE: 3

-continued

```
aattgctaga ctaggatccc ccgtgctgca gaaccgagcg gctattgact tcttgctcct    60
agctcacggc catggctgtg aggacattgc gggaatgtgt tgtttcaatc tgagtgatca   120
cagtgagtct atacagaaga agttccagct aatgaaggaa catgtcaata agatcggcgt   180
gaacaacgac ccaatcggaa gttggctgcg aggattattc ggaggaatag gagaatgggc   240
cgtacacttg ctgaaaggac tgcttttggg gcttgtagtt atcttgttgc tagtagtatg   300
cttgccttgc cttttgcaat gtgtatctag tagtattcga agatgattg ataattcact    360
cggctatcgc gaggaatata aaaaaattac aggaggctta taagcagccc gaaagaagag   420
cgtaggcgag ttcttgtatt ccgtgtgata gctggttgga ttggtaattg atcggctggc   480
acgcggaata taggaggtcg ctgaatagta aacttgtaga cttggctaca gcatagagta   540
tcttctgtag ctctgatgac tgctaggaaa taatgctacg gataatgtgg ggagggcaag   600
gcttgcgaat cgggttgtaa cgggcaaggc ttgactgagg ggacaatagc atgtttaggc   660
gaaaagcggg gcttcggttg tacgcggtta ggagtcccct caggatatag tagtttcgct   720
tttgcatagg gagggggacg gattggacga accactgaat tccgcattgc agagatattg   780
tatttaagtg cctagctcga tacaataaac gccatttgac cattcaccac attggtgtgc   840
acctgggttg atggccggac cgttgattcc ctgrcgacta cgagcacatg catgaagcag   900
aaggcttcat ttggtgaccc cgacgtgatc gttaggaat acgcgctcac tggccgtcgt    960
tttacaacgt cgtgactggg aaaaccctgg cgttacccaa cttaatcgcc ttgcagcaca  1020
tccccctttc gccagctggc gtaatagcga agaggcccgc accgatcgcc cttcccaaca  1080
gttgcgcagc ctgaatggcg aatggaaatt gtaagcgtta atattttgtt aaaattcgcg  1140
ttaaattttt gttaaatcag ctcattttt aaccaatagg ccgaaatcgg caaaatccct   1200
tataaatcaa agaatagac cgagataggg ttgagtgttg ttccagtttg gaacaagagt   1260
ccactattaa agaacgtgga ctccaacgtc aaagggcgaa aaaccgtcta tcagggcgat  1320
ggcccactac gtgaaccatc accctaatca gttttttgg ggtcgaggtg ccgtaaagca   1380
ctaaatcgga accctaaagg gagccccga tttagagctt gacggggaaa gccggcgaac   1440
gtggcgagaa aggaagggaa gaaagcgaaa ggagcgggcg ctagggcgct ggcaagtgta  1500
gcggtcacgc tgcgcgtaac caccacaccc gccgcgctta atgcgccgct acagggcgcg  1560
tcaggtggca cttttcgggg aaatgtgcgc ggaacccta tttgtttatt tttctaaata   1620
cattcaaata tgtatccgct catgagacaa taaccctgat aaatgcttca ataatattga  1680
aaaaggaaga gtatgagtat tcaacatttc cgtgtcgccc ttattccctt ttttgcggca  1740
ttttgccttc ctgttttgc tcacccagaa acgctggtga agtaaaaga tgctgaagat   1800
cagttgggtg cacgagtggg ttacatcgaa ctggatctca acagcggtaa gatccttgag  1860
agttttcgcc ccgaagaacg ttttccaatg atgagcactt ttaaagttct gctatgtggc  1920
gcggtattat cccgtattga cgccgggcaa gagcaactcg gtcgccgcat acactattct  1980
cagaatgact tggttgagta ctcaccagtc acagaaaagc atcttacgga tggcatgaca  2040
gtaagagaat tatgcagtgc tgccataacc atgagtgata acactgcggc caacttactt  2100
ctgacaacga tcggaggacc gaaggagcta accgcttttt tgcacaacat ggggatcat   2160
gtaactcgcc ttgatcgttg gaaccgag ctgaatgaag ccataccaaa cgacgagcgt    2220
gacaccacga tgcctgtagc aatggcaaca acgttgcgca aactattaac tggcgaacta  2280
cttactctag cttcccggca acaattaata gactggatgg aggcggataa agttgcagga  2340
ccacttctgc gctcggccct tccggctggc tggtttattg ctgataaatc tggagccggt  2400
```

-continued

| | | | | |
|---|---|---|---|---|
| gagcgtgggt | ctcgcggtat | cattgcagca | ctggggccag | atggtaagcc ctcccgtatc | 2460 |
| gtagttatct | acacgacggg | gagtcaggca | actatggatg | aacgaaatag acagatcgct | 2520 |
| gagataggtg | cctcactgat | taagcattgg | taactgtcag | accaagttta ctcatatata | 2580 |
| ctttagattg | atttaaaact | tcattttttaa | tttaaaagga | tctaggtgaa gatcctttt | 2640 |
| gataatctca | tgaccaaaat | cccttaacgt | gagttttcgt | tccactgagc gtcagacccc | 2700 |
| gtagaaaaga | tcaaggatc | ttcttgagat | ccttttttc | tgcgcgtaat ctgctgcttg | 2760 |
| caaacaaaaa | aaccaccgct | accagcggtg | gtttgtttgc | cggatcaaga gctaccaact | 2820 |
| cttttttccga | aggtaactgg | cttcagcaga | gcgcagatac | caaatactgt ccttctagtg | 2880 |
| tagccgtagt | taggccacca | cttcaagaac | tctgtagcac | cgcctacata cctcgctctg | 2940 |
| ctaatcctgt | taccagtggc | tgctgccagt | ggcgataagt | cgtgtcttac cgggttggac | 3000 |
| tcaagacgat | agttaccgga | taaggcgcag | cggtcgggct | gaacgggggg ttcgtgcaca | 3060 |
| cagcccagct | tggagcgaac | gacctacacc | gaactgagat | acctacagcg tgagctatga | 3120 |
| gaaagcgcca | cgcttcccga | agggagaaag | gcggacaggt | atccggtaag cggcagggtc | 3180 |
| ggaacaggag | agcgcacgag | ggagcttcca | gggggaaacg | cctggtatct ttatagtcct | 3240 |
| gtcgggtttc | gccacctctg | acttgagcgt | cgatttttgt | gatgctcgtc agggggggcgg | 3300 |
| agcctatgga | aaaacgccag | caacgcggcc | ttttacggt | tcctggcctt ttgctggcct | 3360 |
| tttgctcaca | tgttctttcc | tgcgttatcc | cctgattctg | tggataaccg tattaccgcc | 3420 |
| tttgagtgag | ctgataccgc | tcgccgcagc | cgaacgaccg | agcgcagcga gtcagtgagc | 3480 |
| gaggaagcgg | aagagcgccc | aatacgcaaa | ccgcctctcc | ccgcgcgttg gccgattcat | 3540 |
| taatgcagct | ggcacgacag | gtttcccgac | tggaaagcgg | gcagtgagcg caacgcaatt | 3600 |
| aatgtgagtt | agctcactca | ttaggcaccc | caggctttac | actttatgct tccggctcgt | 3660 |
| atgttgtgtg | gaattgtgag | cggataacaa | tttcacacag | gaaacagcta tgaccatgat | 3720 |
| tacgccaagc | gcgcattggt | aattgatcgg | ctggcacgcg | gaatatagga ggtcgctgaa | 3780 |
| tagtaaactt | gtagacttgg | ctacagcata | gagtatcttc | tgtagctctg atgactgcta | 3840 |
| ggaaataatg | ctacggataa | tgtggggagg | gcaaggcttg | cgaatcgggt tgtaacgggc | 3900 |
| aaggcttgac | tgagggggaca | atagcatgtt | taggcgaaaa | gcggggcttc ggttgtacgc | 3960 |
| ggttaggagt | ccccctcagga | tatagtagtt | tcgcttttgc | atagggaggg ggaaatgtag | 4020 |
| tcttatgcaa | tactcttgta | gtcttgcaac | atgcttatgt | aacgatgagt tagcaacatg | 4080 |
| ccttataagg | agagaaaaag | caccgtgcat | gccgattggt | gggagtaagg tggtatgatc | 4140 |
| gtggtatgat | cgtgccttgt | taggaaggca | acagacgggt | ctaacacgga ttggacgaac | 4200 |
| cactgaattc | cgcattgcag | agatattgta | tttaagtgcc | tagctcgata caataaacgc | 4260 |
| catttgacca | ttcaccacat | tggtgtgcac | ctgggttgat | ggccggaccg ttgattccct | 4320 |
| grcgactacg | agcacatgca | tgaagcagaa | ggcttcattt | ggtgaccccg acgtgatcgt | 4380 |
| tagggaatag | tggtcggcca | caggcggcgt | ggcgatcctg | tcctcatccg tctcgcttat | 4440 |
| tcggggagcg | gacgatgacc | ctagtagagg | gggctgcggc | ttaggagggc agaagctgag | 4500 |
| tggcgtcgga | gggagcccta | ctgcaggggg | ccaacatacc | ctaccgagaa ctcagagagt | 4560 |
| cgttggaaga | cgggaaggaa | gcccgacgac | tgagcggtcc | accccaggcg tgattccggt | 4620 |
| tgctctgcgt | gattccggtc | gcccggtgga | tcaagcatgg | aagccgtcat aaaggtgatt | 4680 |
| tcgtccgcgt | gtaagaccta | ttgcgggaaa | acctctcctt | ctaagaagga ataggggct | 4740 |
| atgttgtccc | tgttacaaaa | ggaagggttg | cttacgtccc | cctcagactt atattccccg | 4800 |

```
gggtcctggg atcccattac cgcggcgctc tctcagcggg ctatggtact tggaaaatcg    4860
ggagagttaa aaacctgggg attggttttg ggggcattga aggcggctcg agatccggta    4920
ccttcaaata ctacaagtga aaagtgtttg cttaaacatg ttttatttat gattaaagga    4980
acaaaagagc acattcacaa gacccattac atatgggtac aaggaaaaca atttgaatag    5040
taatatacca tatttgccaa cataccatga ttgagtcaaa gtttagggag aaatgtgaat    5100
tataagattt ttataatgca tctttaggaa gtcaggaaga gccttgtagt atcaggaaca    5160
cagagaacaa gcaattgcct tgtcagcata ggaatggttg gtgacagttg ataatttaat    5220
ctgagagatt ttgagtgact aattctggag cagcttggtc atacagatat ctggcttaat    5280
tggaaggctg catttttccc ccataaacct tctgctgatg tatcaggttg cattttcag     5340 tgtgatgact cagtactgtg agtccaattt cattcctta agccttcatc catgagttac      5400
cagtattact ctgtgtaaag gaaaagtgaa ttgcacctgt tctcacagtg taatttcttt    5460
ctgatttttt ttctagatta agctccagct tttatgaagt ctggatgcag cagataacat    5520 actttcatt ttaccctga tactacagtg ctctgggtct tgttggaagg acagagttt       5580 ttcagctttc ttctttgaat tcctcattta cccggagaca gggagaggct cttctgcgtg    5640
tagtggttgt gcagagcctc atgcatcacg gagcatgaga agacgttccc ctgctgccac    5700
ctgctcttgt ccacggtgag cttgctgtag aggaagaagg agccgtcgga gtccagcacg    5760
ggaggcgtgg tcttgtagtt gttctccggc tgcccattgc tctcccactc cacggcgatg    5820
tcgctgggat agaagccttt gaccaggcag gtcaggctga cctggttctt ggtcagctca    5880
tcccgggatg ggggcagggt gtacacctgt ggttctcggg gctgcccttt ggctttggag    5940
atggttttct cgatggggc tgggagggct ttgttggaga ccttgcactt gtactccttg     6000
ccattcagcc agtcctggtg caggacggtg aggacgctga ccacccggta cgtgctgttg    6060
tactgctcct cccgcggctt tgtcttggca ttatgcacct cccgccgtc cacgtaccag      6120 ttgaacttga cctcagggtc ttcgtggctc acgtccacca ccacgcatgt gacctcaggg    6180
gtccgggaga tcatgagggt gtccttgggt tttgggggga agaggaagac tgacgatccc    6240
cccaggagtt caggtgctgg ggacggtggg gatgtgtgag ttttgtcaga agatttgggc    6300
tcctgatcag aatctgggca cggttctgga tcaattacat aaatctgggt tccgttgcct    6360
atgcccaggt agtatggcgg tgggtacatg agctccacct tgcagatgta gagtcccgtg    6420
tccatggccc tcagtccttg gatagtgagg ttcacttgat ttccactgga ggtgcccgtg    6480
cagatggaat catctaggaa ggtcaactca ttccccatca tgtaggttgc cgcacagact    6540
tcagtcacct ggctgtcagc ctgccgaagc actgtcaccc ggacctcagt ggctttgcct    6600
ggagatgcat actcacacac aaagctrgcg atgcctcggc tgctggccag taccacagca    6660
ggctgggcca cgtgcattgc catgctcgcc atgcttggaa acaggagtgc aaggaccaga    6720
ctgagcagcg tcctctgtgt gagcagtaca cccatggtga actctgagtt gtctagagca    6780
aacagcagaa cagtgaaaat gtaaggatgg aatgctgtac atagtaccat gcagggtact    6840
ctatggtagg ctacaacagt aaattacgag cagtttttag gcaattaaat gttaacaagt    6900
agttttaaag taattctgtg gtaatgtgtc tgttgctata tccacctctc atgtgcatgt    6960
tcaaaaccat attcataaat ctatttatgt atttgcattc agttgtcttt tgggtagcaa    7020
actgtcccag aagccagttg cctctacata tttttgttca gtgaaagcta gaattcattg    7080 atactttca gtacctctga ttaaaacaca atctgatagg cttgcaaaac tggaaattca     7140
aagagcaaat ttcagtaaac tttaggtttg acagatata tgagaaagca gaggcttgct     7200
```

```
gactatttta tttcttattt ttattcccta aaaataaatg tagagaaata tctgtttgtt    7260
gcacactact tgctatgagt agatcttcaa aagtatttt  accttttgttt tggtgatggc   7320 agaatagata aggaatgtaa tttatatggg gtcatgtagt ctaggagaaa gacacgcatg    7380
taattcatat tctgctctat tgcactttca ggtatggttt gctttgctca aagatatgca   7440
tgtgtactgt agtataaact ttctgtggag ttaaatttta gtggtgacat tcagacagaa   7500
gagaaatgca gacatgataa aatagcaatg tttactataa aacagagcca ctgaatgaat   7560
tcttgttcat gacatagacc aatagaagat ttatacttgt tctgtctgtt tctattataa   7620
agagctgaac tgtacaacta ttgtatagcc agtgtgctta tataaagcac agcttttgga   7680
gccagcatga atctagttgc tttcctgaga tttatataat ctgtgaaagt cagaagtcct   7740
tcagagccca gcccttttata tgcgtactga gtgctgggc  ctcaggattg gattttctgt   7800
attaaacccc tcaaaagttt ttactgacca cgtgtgtgag tatacacaca cacattttttc   7860 tcattttcctt ttctgtatat aagttcacat gtatctatta ttgtaagaat atacgtttat   7920
gcacccccca cattttttatc ttgtgtagtg atcagcagct gcactttgca ggaattaaac    7980
ttctagagaa ttttcacatt aaaataactc cccagaattc actgaacacc atgattttgc   8040
tctctgtgca ctctgtaggg ctagaagtta atcaagcaaa ctgcaaagca tatcagatag   8100
tgaacgacag gataagatgt tctgaaatta aaaacatatt ttaagcacaa agaataagcc   8160
tcctgaaaac aaacacaaag cttttacaca taataaaata gtgcagaatg catacacagg   8220
tgagaagttt ttatagggg  tatcacgcag gtacttcacc cttaaagata caacacatag    8280
cacaataatt gttaattttt taaagtttag gtgcaagtaa gagctaatat agagagaagg   8340
taattccaga gagttgctta cctttcgagc ttgactgcta aaggcaatac agcttttctag   8400 ctgtatgtac agacactggc tgagccctgg ggaatatata gtctgaattg tgacccaccc   8460
acaggttccc ttcagaagtt tgacctttga caccatagaa atcatttaat gggattgggt   8520
tagattttag tttcaatagg tccatttttgg attgaatgga gagcaaatat tagttttttaa   8580 ttctgggtaa caatgtgttt tctgcctgtt ctgctaatcc atcaggactg ttggatggga    8640
gagaagactg ggaaatattg ctcatgttcc attgagcttc agttacaacc agataatggg   8700
atctttaaga aaacagaaaa atgtgggaac cttggagatg gaaaacataa ttagcaatta   8760
ttagttagtg tgcttattac tatggttgta gtaacagacc agaagtctgt ttcatttgat   8820
ccttcttgta tgtacaatgt gcatctgagc cacgctagac aggacataaa tgagaacaag   8880
acttgaccta ttattttctt gacaaaatag gagaaataaa gaagcgtgca tgtgaaggag   8940
ccaactgaga ctagagtgaa gagcagacac actttctttc ctatagttgg aatatttaaa    9000
tctatctttt tatgggtgtg aatgctttat aacaaacttt tattctgagg atacagcaaa   9060
acatagctcc atacaatgca aaacaatact caatttcaaa tgtgtttatg atatgaactt   9120
gcagtgttcc tcaaagatct tccatgaata acttaatggc ctggcagatg acagaggaat   9180
tgtgaaattc agctggagga gtgttcatgg ttcgagggac aatcataata tacaatagca    9240
aatatatttc agttatagaa gctattgttc tgtattgaaa taatagaatt gacaaacagt    9300
aaagaaacca ttctgacctc tgtaaagcac tgtttgattt aaaaatgggg gaaaaaagta   9360
caacataatt cttcaggaca tacatagaga tcactgcaat ctctgttaag cagaattact   9420
ttcctatacc actagctgaa gtttagtcag tgccattttc ttttgtttct ctccttcctt   9480
ttgtgaaaac atatatactg tggaaatcta cattctcctt gccaagtctg aggacttaag   9540
acaagatggt agtgcaaata atatttttt  gctggatgtc tacaccacag gtatcaactg    9600
```

```
atttttttttg tttcatttttg ttttaatca cgtctttgc ttctatttca gccactaaga    9660
aagtctgaaa atcttgcctg cttttgtga tgatagatgt gcttcccagt aaatgttatc    9720
tctacctatg aaatgcatgt cagtctgcag aaagagaaag gagattggga ataggttttc    9780
tcagatgcac ttctctgtca tctggtgtca atcaaacact aataatttgt gtatagatat    9840
cttatatata tatatatatt tggaatttgc aggttggcat agttcagata gtcctgtcac    9900
attgtaatat cctggtgaga taacaaggaa aagagagacc gtttcggctc ttactaaggc    9960
agggaactgc ttaccagaca gggaggttct ggagatgaca tccagcatga aaagcacact   10020
tccaaatact taaaggtatc aagtctaact tgtcagacag gctccagaat aacttctgtc   10080
ctaatgctac agaaaagggg gaaggtatcc accatggcca aaattgtcag ccattttgtc   10140
tcagcaaaca gcagatctgg tcagtaagga caagattctt ccaaagcaac catgccatat   10200
ataattaagc atgtgtaatt aattaataaa aaatataatt tagtgtattt cctcctttgg   10260
atgttatgaa gaaatgcttt tattaacaat tcaccataat ctgtcctaag agtagtgaat   10320
aacaacaggc tgcttctcac cctgtggttg ggtgtaccag tgagccagag ctaaacgcca   10380
cgtttcctct tttgtatccc atagcagaga gggtctccat ttcatttctg tagctcagaa   10440
agttgtagtg gatttacact acaagttgtg gtagtggagg tctgccggag tggcctctgt   10500
gaacagagcc cagcagctgt cccgtgtcct caaagggag ctgccactgg ccagagctga    10560
gccagtgatc gatgctagat gtacctcagg aggagcaata tgtaagaaca actgctgtac   10620
aatggtagtt gggagaggtg agtgagaaaa tgtgagagaa acagccctga tgacactgag   10680
gtcagtgcgg aggagggcag gaggtgttcc aggtgtagaa cagaagttcc ctgcagccca   10740
agagaggccc atggtggagc actctgaccc tctgcagccc atggtatatc atataaacct   10800
cagttctgtg acattatttt aactccatat cccttttctg ttcagggtca ctttgagttc   10860
acagccattt ctttatattt ctccaatatc agccttccat tgctacatat gagacttgga   10920
cagtacatct gattcagtca aatctgcctt cagaacgtcc ctgaagccct tcttagacag   10980
tctcaattct ccttcccttc atctctttta tcatacatgg accacggacc tgtccagacc   11040
tgagtcatat gtccatcttt acgtccatct ctatgtcttg tactttaaga caaataaaat   11100
atcaaggaaa ttgatgcagt tatgtcagtt atcactgtca tagtatcgtg ctgcaaatat   11160
aagatgagaa tgatcccaaa ggctttttaa agctgctcta tttgacttcc acatagtgtc   11220
ctgattccag acctacagaa cagttttgta tgcatttgac ttgcagagct ttgttttgtg   11280
agtcttataa aagccatttt tcctctccaa gaagtagccg gtggtttaaa acaatgtaga   11340
ttaagtgtgg agcatgagaa tttctgcttt tctgtcagat gagaaggata tactacactc   11400
tttcccaatg gaagaccagc tgcaagcaac aaaaattgtc catgaacaaa tgagatcttg   11460
atcagaacag gctgtcatca tagtgttgtc agcatacctg catagttggt ttgacttggg   11520
ggtctagaga gagtaagcaa caatcttctt gcagttggaa ggttacctgg gataggtggc   11580
aatggattgc cctgcccagc acagctgtgc aaagcagtac aaatagtttt gtcacacatt   11640
gtttgacaat gcttgtccca agaaaaggtc agctaaggct ctgctgccct ttcctatgcc   11700
aggcatttca ttgtgggtct gtccctaaac caacagtctc atgaataaag actcggagac   11760
ctgaaagtta taaaagcact ttttatccaa aaggatatga agtccaggtg agctcacagg   11820
tcaaagcctc ttatccaatc actaaaacct actcagaact tgactcga                 11868
```

<210> SEQ ID NO 4
<211> LENGTH: 10021

```
<212> TYPE: DNA
<213> ORGANISM: Artificial Sequence
<220> FEATURE:
<223> OTHER INFORMATION: pSIN-3.9-OM-CTLA4-Fc Vector

<400> SEQUENCE: 4
ctagactagg atccccgtg ctgcagaacc gagcggctat tgacttcttg ctcctagctc      60
acggccatgg ctgtgaggac attgcgggaa tgtgttgttt caatctgagt gatcacagtg     120
agtctataca gaagaagttc cagctaatga aggaacatgt caataagatc ggcgtgaaca     180
acgacccaat cggaagttgg ctgcgaggat tattcggagg aataggagaa tgggccgtac     240
acttgctgaa aggactgctt ttggggcttg tagttatctt gttgctagta gtatgcttgc     300
cttgcctttt gcaatgtgta tctagtagta ttcgaaagat gattgataat tcactcggct     360
atcgcgagga atataaaaaa attacaggag cttataagc agcccgaaag aagagcgtag      420
gcgagttctt gtattccgtg tgatagctgg ttggattggt aattgatcgg ctggcacgcg     480
gaatatagga ggtcgctgaa tagtaaactt gtagacttgg ctacagcata gagtatcttc     540
tgtagctctg atgactgcta ggaaataatg ctacggataa tgtggggagg gcaaggcttg     600
cgaatcgggt tgtaacgggc aaggcttgac tgagggaca atagcatgtt taggcgaaaa      660
gcggggcttc ggttgtacgc ggttaggagt ccctcagga tatagtagtt tcgcttttgc      720
atagggaggg ggacggattg gacgaaccac tgaattccgc attgcagaga tattgtattt     780
aagtgcctag ctcgatacaa taaacgccat ttgaccattc accacattgg tgtgcacctg     840
ggttgatggc cggaccgttg attccctgrc gactacgagc acatgcatga agcagaaggc     900
ttcatttggt gaccccgacg tgatcgttag ggaatacgcg ctcactggcc gtcgttttac     960
aacgtcgtga ctgggaaaac cctggcgtta cccaacttaa tcgccttgca gcacatcccc    1020
ctttcgccag ctggcgtaat agcgaagagg cccgcaccga tcgcccttcc aacagttgc     1080 gcagcctgaa tggcgaatgg aaattgtaag cgttaatatt ttgttaaaat tcgcgttaaa    1140 ttttttgttaa atcagctcat tttttaacca ataggccgaa atcggcaaaa tcccttataa    1200
atcaaaagaa tagaccgaga tagggttgag tgttgttcca gtttggaaca agagtccact    1260
attaaagaac gtggactcca acgtcaaagg gcgaaaaacc gtctatcagg gcgatggccc    1320
actacgtgaa ccatcaccct aatcaagttt tttggggtcg aggtgccgta aagcactaaa    1380
tcggaaccct aaagggagcc cccgatttag agcttgacgg ggaaagccgg cgaacgtggc    1440
gagaaaggaa gggaagaaag cgaaaggagc gggcgctagg gcgctggcaa gtgtagcggt    1500
cacgctgcgc gtaaccacca cacccgccgc gcttaatgcg ccgctacagg gcgcgtcagg    1560
tggcactttt cggggaaatg tgcgcggaac ccctatttgt ttatttttct aaatacattc    1620
aaatatgtat ccgctcatga caataaacc ctgataaatg cttcaataat attgaaaaag    1680
gaagagtatg agtattcaac atttccgtgt cgcccttatt ccctttttg cggcatttg      1740 ccttcctgtt tttgctcacc cagaaacgct ggtgaaagta aagatgctg aagatcagtt     1800 gggtgcacga gtgggttaca tcgaactgga tctcaacagc ggtaagatcc ttgagagttt    1860
tcgccccgaa gaacgttttc caatgatgag cacttttaaa gttctgctat gtggcgcggt    1920
attatcccgt attgacgccg gcaagagca actcggtcgc cgcatacact attctcagaa     1980
tgacttggtt gagtactcac cagtcacaga aaagcatctt acggatggca tgacagtaag    2040
agaattatgc agtgctgcca taaccatgag tgataacact gcggccaact tacttctgac    2100
aacgatcgga ggaccgaagg agctaaccgc ttttttgcac aacatggggg atcatgtaac    2160
tcgccttgat cgttgggaac cggagctgaa tgaagccata ccaaacgacg agcgtgacac    2220
```

```
cacgatgcct gtagcaatgg caacaacgtt gcgcaaacta ttaactggcg aactacttac   2280
tctagcttcc cggcaacaat taatagactg gatggaggcg gataaagttg caggaccact   2340
tctgcgctcg gcccttccgg ctggctggtt tattgctgat aaatctggag ccggtgagcg   2400
tgggtctcgc ggtatcattg cagcactggg gccagatggt aagccctccc gtatcgtagt   2460
tatctacacg acgggagtc aggcaactat ggatgaacga aatagacaga tcgctgagat   2520
aggtgcctca ctgattaagc attggtaact gtcagaccaa gtttactcat atatacttta   2580
gattgattta aaacttcatt tttaatttaa aaggatctag gtgaagatcc ttttgataa   2640 tctcatgacc aaaatccctt aacgtgagtt ttcgttccac tgagcgtcag accccgtaga   2700
aaagatcaaa ggatcttctt gagatccttt tttctgcgc gtaatctgct gcttgcaaac   2760
aaaaaaacca ccgctaccag cggtggtttg tttgccggat caagagctac caactctttt   2820
tccgaaggta actggcttca gcagagcgca gataccaaat actgtccttc tagtgtagcc   2880
gtagttaggc caccacttca agaactctgt agcaccgcct acatacctcg ctctgctaat   2940
cctgttacca gtggctgctg ccagtggcga taagtcgtgt cttaccgggt tggactcaag   3000
acgatagtta ccggataagg cgcagcggtc gggctgaacg gggggttcgt gcacacagcc   3060
cagcttggag cgaacgacct acaccgaact gagatacc ta cagcgtgagc tatgagaaag   3120
cgccacgctt cccgaaggga gaaaggcgga caggtatccg gtaagcggca gggtcggaac   3180
aggagagcgc acgagggagc ttccagggg aaacgcctgg tatctttata gtcctgtcgg   3240
gtttcgccac ctctgacttg agcgtcgatt tttgtgatgc tcgtcagggg gcggagcct   3300 atggaaaaac gccagcaacg cggcctttt acggttcctg gccttttgct ggccttttgc   3360
tcacatgttc tttcctgcgt tatccctga ttctgtggat aaccgtatta ccgcctttga   3420
gtgagctgat accgctcgcc gcagccgaac gaccgagcgc agcgagtcag tgagcgagga   3480
agcggaagag cgcccaatac gcaaaccgcc tctccccgcg cgttggccga ttcattaatg   3540
cagctggcac gacaggtttc ccgactggaa agcgggcagt gagcgcaacg caattaatgt   3600
gagttagctc actcattagg caccccaggc tttacacttt atgcttccgg ctcgtatgtt   3660
gtgtggaatt gtgagcggat aacaatttca cacaggaaac agctatgacc atgattacgc   3720
caagcgcgca ttggtaattg atcggctggc acgcggaata taggaggtcg ctgaatagta   3780
aacttgtaga cttggctaca gcatagagta tcttctgtag ctctgatgac tgctaggaaa   3840
taatgctacg gataatgtgg ggagggcaag gcttgcgaat cgggttgtaa cgggcaaggc   3900
ttgactgagg ggacaatagc atgtttaggc gaaaagcggg gcttcggttg tacgcggtta   3960 ggagtccct caggatatag tagtttcgct tttgcatagg gaggggaaa tgtagtctta   4020 tgcaatactc ttgtagtctt gcaacatgct tatgtaacga tgagttagca acatgcctta   4080
taaggagaga aaaagcaccg tgcatgccga ttggtgggag taaggtggta tgatcgtggt   4140
atgatcgtgc cttgttagga aggcaacaga cgggtctaac acggattgga cgaaccactg   4200
aattccgcat tgcagagata ttgtatttaa gtgcctagct cgatacaata aacgccattt   4260
gaccattcac cacattggtg tgcacctggg ttgatggccg gaccgttgat ccctgrcga   4320 ctacagagcac atgcatgaag cagaaggctt catttggtga ccccgacgtg atcgttaggg   4380
aatagtggtc ggccacaggc ggcgtggcga tcctgtcctc atccgtctcg cttattcggg   4440
gagcggacga tgaccctagt agagggggct gcggcttagg agggcagaag ctgagtggcg   4500
tcggagggag ccctactgca gggggccaac atacctac gagaactcag agagtcgttg   4560
gaagacggga aggaagcccg acgactgagc ggtccacccc aggcgtgatt ccggttgctc   4620
```

```
tgcgtgattc cggtcgcccg gtggatcaag catggaagcc gtcataaagg tgatttcgtc    4680
cgcgtgtaag acctattgcg ggaaaacctc tccttctaag aaggaaatag gggctatgtt    4740
gtccctgtta caaaggaag ggttgcttac gtcccctca gacttatatt ccccggggtc      4800
ctgggatccc attaccgcgg cgctctctca gcgggctatg gtacttggaa aatcgggaga    4860
gttaaaaacc tggggattgg ttttgggggc attgaaggcg gctcgaggtc gacggtatcg    4920
ataagcttgc agtccaaggc tttgtctgtg tacccagtga aatccttcct ctgttacata    4980
aagcccagat aggactcaga aatgtagtca ttccagcccc cctcttcctc agatctggag    5040
cagcacttgt ttgcagccag tcctccccaa aatgcacaga cctcgccgag tggagggaga    5100
tgtaaacagc gaaggttaat tacctccttg tcaaaaacac tttgtggtcc atagatgttt    5160
ctgtcaatct tacaaaacag aaccgagagg cagcgagcac tgaagagcgt gttcccatgc    5220
tgagttaatg agacttggca gctcgctgtg cagagatgat ccctgtgctt catgggaggc    5280
tgtaacctgt ctccccatcg ccttcacacc gcagtgctgt cctggacacc tcaccctcca    5340
taagctgtag gatgcagctg cccagggatc aagagacttt tcctaaggct cttaggactc    5400
atctttgccg ctcagtagcg tgcagcaatt actcatccca actatactga atgggtttct    5460
gccagctctg cttgtttgtc aataagcatt tcttcatttt gcctctaagt ttctctcagc    5520
agcaccgctc tgggtgacct gagtggccac ctggaacccg aggggcacag ccaccacctc    5580
cctgttgctg ctgctccagg gactcatgtg ctgctggatg gggggaagca tgaagttcct    5640
cacccagaca cctgggttgc aatggctgca gcgtgctctt cttggtatgc agattgtttc    5700
cagccattac ttgtagaaat gtgctgtgga agcccttgt atctctttct gtggcccttc     5760
agcaaaagct gtgggaaagc tctgaggctg ctttcttggg tcgtggagga attgtatgtt    5820
ccttctttaa caaaaattat ccttaggaga gagcactgtg caagcattgt gcacataaaa    5880
caattcaggt tgaaagggct ctctggaggt ttccagcctg actactgctc gaagcaaggc    5940
caggttcaaa gatggctcag gatgctgtgt gccttcctga ttatctgtgc caccaatgga    6000
ggagattcac agccactctg cttcccgtgc cactcatgga gaggaatatt cccttatatt    6060
cagatagaat gttatccttt agctcagcct tccctataac cccatgaggg agctgcagat    6120
ccccatactc tccccttctc tggggtgaag gccgtgtccc ccagcccccc ttcccaccct    6180
gtgccctaag cagcccgctg gcctctgctg gatgtgtgcc tatatgtcaa tgcctgtcct    6240
tgcagtccag cctgggacat ttaattcatc accagggtaa tgtggaactg tgtcatcttc    6300
ccctgcaggg tacaaagttc tgcacggggt cctttcggtt caggaaaacc ttcactggtg    6360
ctacctgaat caagctctat ttaataagtt cataagcaca tggatgtgtt ttcctagaga    6420
tacgttttaa tggtatcagt gatttttatt tgctttgttg cttacttcaa acagtgcctt    6480
tgggcaggag gtgagggacg ggtctgccgt tggctctgca gtgatttctc caggcgtgtg    6540
gctcaggtca gatagtggtc actctgtggc cagaagaagg acaaagatgg aaattgcaga    6600
ttgagtcacg ttaagcaggc atcttggagt gatttgaggc agtttcatga aagagctacg    6660
accacttatt gttgttttcc ccttttacaa cagaagtttt catcaaaata acgtggcaaa    6720
gcccaggaat gtttgggaaa agtgtagtta aatgttttgt aattcatttg tcggagtgct    6780
accagctaag aaaaaagtcc tacctttggt atggtagtcc tgcagagaat acaacatcaa    6840
tattagtttg gaaaaaaaca ccaccaccac cagaaactgt aatggaaaat gtaaaccaag    6900
aaattccttg ggtaagagag aaaggatgtc gtatactggc caagtcctgc ccagctgtca    6960
gcctgctgac cctctgcagt tcaggaccat gaaacgtggc actgtaagac gtgtcccctg    7020
```

```
cctttgcttg cccacagatc tctgcccttg tgctgactcc tgcacacaag agcatttccc    7080
tgtagccaaa cagcgattag ccataagctg cacctgactt tgaggattaa gagtttgcaa    7140
ttaagtggat tgcagcagga gatcagtggc agggttgcag atgaaatcct tttctagggg    7200
tagctaaggg ctgagcaacc tgtcctacag cacaagccaa accagccaag ggttttcctg    7260
tgctgttcac agaggcaggg ccagctggag ctggaggagg ttgtgctggg acccttctcc    7320
ctgtgctgag aatggagtga tttctgggtg ctgttcctgt ggcttgcact gagcagctca    7380
agggagatcg gtgctcctca tgcagtgcca aaactcgtgt ttgatgcaga agatggatg    7440
tgcacctccc tcctgctaat gcagccgtga gcttatgaag gcaatgagcc ctcagtgcag    7500
caggagctgt agtgcactcc tgtaggtgct agggaaaatc tctggttccc agggatgcat    7560
tcataagggc aatatatctt gaggctgcgc caaatctttc tgaaatattc atgcgtgttc    7620
ccttaattta tagaaacaaa cacagcagaa taattattcc aatgcctccc ctcgaaggaa    7680
acccatattt ccatgtagaa atgtaaccta tatacacaca gccatgctgc atccttcaga    7740
acgtgccagt gctcatctcc catggcaaaa tactacaggt attctcacta tgttggacct    7800
gtgaaaggaa ccatggtaag aaacttcggt taaaggtatg gctgcaaaac tactcatacc    7860
aaaacagcag agctccagac ctcctcttag gaaagagcca cttggagagg gatggtgtga    7920
aggctggagg tgagagacag agcctgtccc agttttcctg tctctatttt ctgaaacgtt    7980
tgcaggagga aaggacaact gtactttcag gcatagctgg tgccctcacg taaataagtt    8040
ccccgaactt ctgtgtcatt tgttcttaag atgctttggc agaacacttt gagtcaattc    8100
gcttaactgt gactaggtct gtaaataagt gctccctgct gataaggttc aagtgacatt    8160
tttagtggta tttgacagca tttaccttgc tttcaagtct tctaccaagc tcttctatac    8220
ttaagcagtg aaaccgccaa gaaacccttc cttttatcaa gctagtgcta aataccatta    8280
acttcatagg ttagatacgg tgctgccagc ttcacctggc agtggttggt cagttctgct    8340
ggtgacaaag cctccctggc ctgtgctttt acctagaggt gaatatccaa gaatgcagaa    8400
ctgcatggaa agcagagctg caggcacgat ggtgctgagc cttagctgct tcctgctggg    8460
agatgtggat gcagagacga atgaaggacc tgtcccttac tcccctcagc attctgtgct    8520
atttaggggtt ctaccagagt ccttaagagg tttttttttt ttttggtcca aaagtctgtt    8580
tgtttggttt tgaccactga gagcatgtga cacttgtctc aagctattaa ccaagtgtcc    8640
agccaaaatc aattgcctgg gagacgcaga ccattacctg gaggtcagga cctcaataaa    8700
tattaccagc ctcattgtgc cgctgacaga ttcagctggc tgctccgtgt tccagtccaa    8760
cagttcggac gccacgtttg tatatatttg caggcagcct cgggggggacc atctcaggag    8820
cagagcaccg gcagccgcct gcagagccgg gcagtacctc aacatgggtg tactgctcac    8880
acagaggacg ctgctcagtc tggtccttgc actcctgttt ccaagcatgg cgagcatggc    8940
aatgcacgtg gcccagcctg ctgtggtact ggccagcagc cgaggcatcg cyagctttgt    9000
gtgtgagtat gcatctccag gcaaagccac tgaggtccgg gtgacagtgc ttcggcaggc    9060
tgacagccag gtgactgaag tctgtgcggc aacctacatg atggggaatg agttgacctt    9120
cctagatgat tccatctgca cgggcacctc cagtggaaat caagtgaacc tcactatcca    9180
aggactgagg gccatggaca cgggactcta catctgcaag gtggagctca tgtacccacc    9240
gccatactac ctgggcatag gcaacggaac ccagatttat gtaattgatc cagaaccgtg    9300
cccagattct gatcaggagc ccaaatcttc tgacaaaact cacacatccc caccgtcccc    9360
agcacctgaa ctcctggggg gatcgtcagt cttcctcttc cccccaaaac ccaaggacac    9420
```

-continued

```
cctcatgatc tcccggaccc ctgaggtcac atgcgtggtg gtggacgtga gccacgaaga    9480
ccctgaggtc aagttcaact ggtacgtgga cggcgtggag gtgcataatg ccaagacaaa    9540
gccgcgggag gagcagtaca acagcacgta ccgggtggtc agcgtcctca ccgtcctgca    9600
ccaggactgg ctgaatggca aggagtacaa gtgcaaggtc tccaacaaag ccctcccagc    9660
ccccatcgag aaaaccatct ccaaagccaa agggcagccc cgagaaccac aggtgtacac    9720
cctgccccca tcccgggatg agctgaccaa gaaccaggtc agcctgacct gcctggtcaa    9780
aggcttctat cccagcgaca tcgccgtgga gtgggagagc aatgggcagc cggagaacaa    9840
ctacaagacc acgcctcccg tgctggactc cgacggctcc ttcttcctct acagcaagct    9900
caccgtggac aagagcaggt ggcagcaggg gaacgtcttc tcatgctccg tgatgcatga    9960
ggctctgcac aaccactaca cgcagaagag cctctccctg tctccgggta atgaggaat   10020 t                                                                  10021
```

<210> SEQ ID NO 5
<211> LENGTH: 378
<212> TYPE: PRT
<213> ORGANISM: Artificial Sequence
<220> FEATURE:
<223> OTHER INFORMATION: Human lysosomal acid lipase

<400> SEQUENCE: 5

```
Ser Gly Gly Lys Leu Thr Ala Val Asp Pro Glu Thr Asn Met Asn Val
1               5                   10                  15

Ser Glu Ile Ile Ser Tyr Trp Gly Phe Pro Ser Glu Glu Tyr Leu Val
            20                  25                  30

Glu Thr Glu Asp Gly Tyr Ile Leu Cys Leu Asn Arg Ile Pro His Gly
        35                  40                  45

Arg Lys Asn His Ser Asp Lys Gly Pro Lys Pro Val Val Phe Leu Gln
    50                  55                  60

His Gly Leu Leu Ala Asp Ser Ser Asn Trp Val Thr Asn Leu Ala Asn
65                  70                  75                  80

Ser Ser Leu Gly Phe Ile Leu Ala Asp Ala Gly Phe Asp Val Trp Met
                85                  90                  95

Gly Asn Ser Arg Gly Asn Thr Trp Ser Arg Lys His Lys Thr Leu Ser
            100                 105                 110

Val Ser Gln Asp Glu Phe Trp Ala Phe Ser Tyr Asp Glu Met Ala Lys
        115                 120                 125

Tyr Asp Leu Pro Ala Ser Ile Asn Phe Ile Leu Asn Lys Thr Gly Gln
    130                 135                 140

Glu Gln Val Tyr Tyr Val Gly His Ser Gln Gly Thr Thr Ile Gly Phe
145                 150                 155                 160

Ile Ala Phe Ser Gln Ile Pro Glu Leu Ala Lys Arg Ile Lys Met Phe
                165                 170                 175

Phe Ala Leu Gly Pro Val Ala Ser Val Ala Phe Cys Thr Ser Pro Met
            180                 185                 190

Ala Lys Leu Gly Arg Leu Pro Asp His Leu Ile Lys Asp Leu Phe Gly
        195                 200                 205

Asp Lys Glu Phe Leu Pro Gln Ser Ala Phe Leu Lys Trp Leu Gly Thr
    210                 215                 220

His Val Cys Thr His Val Ile Leu Lys Glu Leu Cys Gly Asn Leu Cys
225                 230                 235                 240

Phe Leu Leu Cys Gly Phe Asn Glu Arg Asn Leu Asn Met Ser Arg Val
                245                 250                 255
```

Asp Val Tyr Thr Thr His Ser Pro Ala Gly Thr Ser Val Gln Asn Met
                260                 265                 270

Leu His Trp Ser Gln Ala Val Lys Phe Gln Lys Phe Gln Ala Phe Asp
            275                 280                 285

Trp Gly Ser Ser Ala Lys Asn Tyr Phe His Tyr Asn Gln Ser Tyr Pro
        290                 295                 300

Pro Thr Tyr Asn Val Lys Asp Met Leu Val Pro Thr Ala Val Trp Ser
305                 310                 315                 320

Gly Gly His Asp Trp Leu Ala Asp Val Tyr Asp Val Asn Ile Leu Leu
                325                 330                 335

Thr Gln Ile Thr Asn Leu Val Phe His Glu Ser Ile Pro Glu Trp Glu
            340                 345                 350

His Leu Asp Phe Ile Trp Gly Leu Asp Ala Pro Trp Arg Leu Tyr Asn
        355                 360                 365

Lys Ile Ile Asn Leu Met Arg Lys Tyr Gln
    370                 375

<210> SEQ ID NO 6
<211> LENGTH: 497
<212> TYPE: PRT
<213> ORGANISM: Artificial Sequence
<220> FEATURE:
<223> OTHER INFORMATION: Human glucocerebrosidase

<400> SEQUENCE: 6

Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125

Ser Ile Arg Thr Tyr Thr Tyr Ala Asp Thr Pro Asp Asp Phe Gln Leu
    130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
    210                 215                 220

Leu Gln Phe Trp Ala Val Thr Ala Glu Asn Glu Pro Ser Ala Gly Leu
225                 230                 235                 240

```
Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
    290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
    370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
    450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp Arg Arg
                485                 490                 495

Gln

<210> SEQ ID NO 7
<211> LENGTH: 29
<212> TYPE: DNA
<213> ORGANISM: Artificial Sequence
<220> FEATURE:
<223> OTHER INFORMATION: BAC 26 Primer-1

<400> SEQUENCE: 7
gcggaattca aagaagaaag ctgaaaaac                                    29

<210> SEQ ID NO 8
<211> LENGTH: 29
<212> TYPE: DNA
<213> ORGANISM: Artificial Sequence
<220> FEATURE:
<223> OTHER INFORMATION: BAC 26 Primer-2

<400> SEQUENCE: 8
gcgggtacct tcaaatacta caagtgaaa                                    29

<210> SEQ ID NO 9
<211> LENGTH: 33
<212> TYPE: DNA
<213> ORGANISM: Artificial Sequence
<220> FEATURE:
```

<223> OTHER INFORMATION: BAC 26-OV Primer 1

<400> SEQUENCE: 9
ggcctcgagt caagttctga gtaggtttta gtg          33

<210> SEQ ID NO 10
<211> LENGTH: 41
<212> TYPE: DNA
<213> ORGANISM: Artificial Sequence
<220> FEATURE:
<223> OTHER INFORMATION: BAC 26-OV Primer 2

<400> SEQUENCE: 10
gcgcgtctct gtctagagca aacagcagaa cagtgaaaat g          41

<210> SEQ ID NO 11
<211> LENGTH: 50
<212> TYPE: DNA
<213> ORGANISM: Artificial Sequence
<220> FEATURE:
<223> OTHER INFORMATION: CTLA-4-Fc Primer 1

<400> SEQUENCE: 11
gcgcgtctca agacaactca gagttcacca tgggtgtact gctcacacag          50

<210> SEQ ID NO 12
<211> LENGTH: 29
<212> TYPE: DNA
<213> ORGANISM: Artificial Sequence
<220> FEATURE:
<223> OTHER INFORMATION: CTLA-4-Fc Primer 2

<400> SEQUENCE: 12
ggcccgggag ttttgtcaga agatttggg          29

<210> SEQ ID NO 13
<211> LENGTH: 21
<212> TYPE: PRT
<213> ORGANISM: Artificial Sequence
<220> FEATURE:
<223> OTHER INFORMATION: Signal Sequence Peptides

<400> SEQUENCE: 13

Met Lys Met Arg Phe Leu Gly Leu Val Val Cys Leu Val Leu Trp Thr
1               5                   10                  15

Leu His Ser Glu Gly
            20

<210> SEQ ID NO 14
<211> LENGTH: 39
<212> TYPE: PRT
<213> ORGANISM: Artificial Sequence
<220> FEATURE:
<223> OTHER INFORMATION: Signal Sequence Peptides

<400> SEQUENCE: 14

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly
        35

COMPOSITION COMPRISING ISOLATED HUMAN CTLA4-FC FUSION PROTEIN PRODUCED IN A TRANSGENIC CHICKEN

RELATED APPLICATION INFORMATION

This application is a continuation-in-part of U.S. patent application Ser. No. 11/973,853, filed Oct. 10, 2007 now abandoned, the disclosure of which is incorporated in its entirety herein by reference, which is a continuation-in-part of U.S. patent application Ser. No. 11/708,598, filed Feb. 20, 2007, now U.S. Pat. No. 7,511,120, issued Mar. 31, 2009, the disclosure of which is incorporated in its entirety herein by reference, which is a continuation-in-part of U.S. patent application Ser. No. 11/370,555, filed Mar. 8, 2006, now U.S. Pat. No. 7,338,654, issued Mar. 4, 2008, the disclosure of which is incorporated in its entirety herein by reference, and is a continuation-in-part of U.S. patent application Ser. No. 11/167,052 filed Jun. 24, 2005, the disclosure of which is incorporated in its entirety herein by reference. This application also claims the benefit of U.S. provisional patent application Nos. 61/192,670, filed Sep. 19, 2008, the disclosure of which is incorporated in its entirety herein by reference, and 61/217,650, filed Jun. 2, 2009, the disclosure of which is incorporated in its entirety herein by reference.

FIELD OF THE INVENTION

The present invention relates to the expression of the exogenous genetic material in avian cells. The invention also relates to transgenic avian species, including chicken, quail and turkey, and to avians which lay eggs containing exogenous proteins, for example pharmaceutical proteins including fusion proteins such as Fc fusion proteins (e.g., CTLA4-Fc) and to the exogenous proteins.

BACKGROUND

Numerous natural and synthetic proteins are used in diagnostic and therapeutic applications and many others are in development or in clinical trials. Current methods of protein production include isolation from natural sources and recombinant production in cell culture. Because of the complexity, high cost and known problems of these methods such as batch failure, efforts have been underway to develop alternatives. For example, methods for producing exogenous proteins in the milk of pigs, sheep, goats, and cows have been reported. These approaches have certain limitations, including long generation times between founder and production herds, extensive husbandry and veterinary costs. Proteins are also being produced using milling and malting processes from barley and rye. However, plant post-translational modifications substantially differ from vertebrate post-translational modifications, which can have a negative effect on the function of the exogenous proteins such as pharmaceutical proteins.

The avian oviduct can also serve as a bioreactor. Successful methods of modifying avian genetic material such that high levels of exogenous proteins are secreted in the oviduct and packaged into eggs allows inexpensive production of large amounts of protein. Several advantages of this approach are: a) short generation times (24 weeks) and rapid establishment of transgenic flocks via artificial insemination; b) readily scaled production by increasing flock sizes to meet production needs; c) post-translational modification of expressed proteins; d) automated feeding and egg collection; e) naturally aseptic egg-whites; and f) reduced processing costs due to the high concentration of protein in the egg white.

Recent developments in avian transgenesis have allowed the modification of avian genomes for exogenous protein production. Germ-line transgenic chickens may be produced by injecting replication-defective retrovirus into the subgerminal cavity of chick blastoderms in freshly laid eggs. See, for example, U.S. Pat. No. 7,511,120, issued Mar. 31, 2009, the disclosure of which is incorporated in its entirety herein by reference; issued U.S. Pat. No. 7,338,654, issued Mar. 4, 2008, the disclosure of which is incorporated in its entirety herein by reference; and US patent publication No. 2008/0064862 published Mar. 13, 2008, the disclosure of which is incorporated in its entirety herein by reference.

Limitations of currently accepted methods of producing therapeutic proteins include the expense of producing the production facilities and batch failure. What is needed are improved methods of producing therapeutic or pharmaceutical proteins such as fusion proteins including novel and improved forms of CTLA4-Fc.

SUMMARY OF THE INVENTION

The invention encompasses novel proteins including fusion proteins (e.g., Fc-fusion proteins) such as CTLA4-Fc produced in an avian, e.g., in an avian oviduct. In addition, the invention includes transgenic avians including those which produce eggs containing the recombinant fusion protein, progeny of the transgenic avians, methods of making the avians and the eggs containing the fusion proteins.

In one particular aspect, the fusion proteins of the invention (e.g., Fc fusion protein) such as CTLA4-Fc are produced and glycosylated in an oviduct cell of the avian. For example, the fusion protein can be produced and glycosylated in a quail or chicken oviduct cell. In one embodiment, the fusion protein is produced and glycosylated in a tubular gland cell of the avian.

In one important aspect, the invention relates to an isolated mixture of fusion protein molecules (e.g., Fc fusion protein molecules) such as CTLA4-Fc molecules comprising a fusion protein molecule of the invention glycosylated with at least one of the following eight structures:

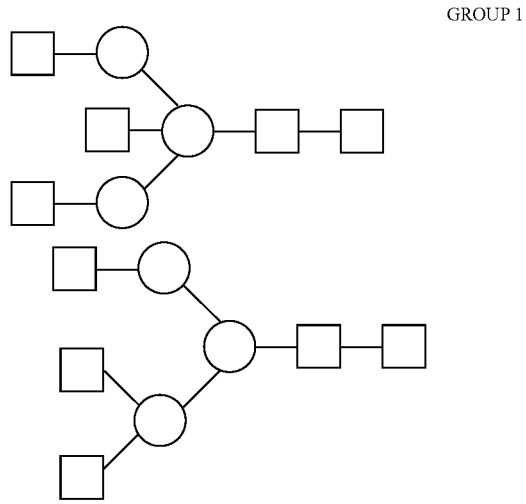

GROUP 1

-continued

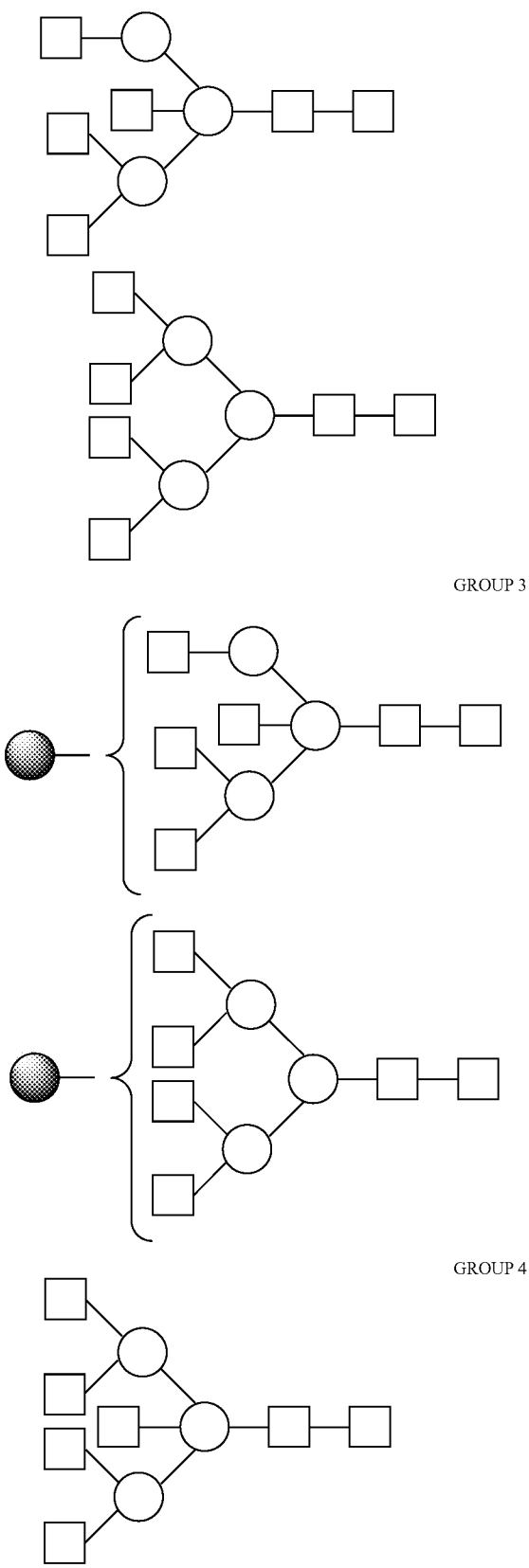

GROUP 2

GROUP 3

GROUP 4

-continued

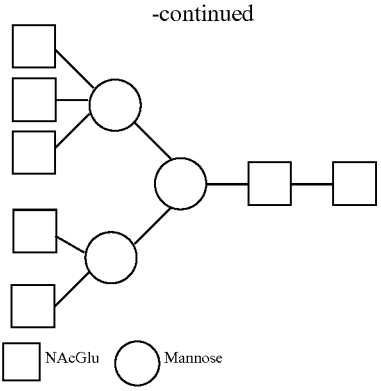

In one embodiment, the isolated mixture of fusion protein molecules (e.g., Fc fusion protein molecules) such as CTLA4-Fc molecules contains one or more fusion protein molecules which contain oligosaccharide structures from at least two of groups 1, 2, 3 and 4.

In another embodiment, the isolated mixture of fusion protein molecules (e.g., Fc fusion protein molecules) such as CTLA4-Fc molecules contains one or more fusion protein molecules which contain oligosaccharide structures from at least three of groups 1, 2, 3 and 4.

In another embodiment, the isolated mixture of fusion protein molecules (e.g., Fc fusion protein molecules) such as CTLA4-Fc molecules contains one or more Fc fusion protein molecules which contain oligosaccharide structures from each of the four groups 1, 2, 3 and 4.

In one embodiment, the CTLA4-Fc molecules of an isolated mixture have the amino acid sequence shown in FIG. 2.

In one embodiment, the fusion protein molecules (e.g., Fc fusion protein molecules) such as CTLA4-Fc molecules of an isolated mixture are in a pharmaceutical composition.

Potential glycosylation sites for CTLA4-Fc are shown in FIG. 2. However, the invention is not limited to glycosylation at any particular site on the fusion protein including CTLA4-Fc. A single potential glycosylation site is shown on an IgG1 Fc sequence shown in FIG. 1, however, the invention is not limited thereto.

The invention is also directed to methods of treatment using the fusion protein molecules (e.g., Fc fusion protein molecules) such as CTLA4-Fc, as is understood in the art.

In one aspect, the invention is directed to fusion protein molecules (e.g., Fc fusion protein molecules) such as CTLA4-Fc molecules obtained from a transgenic avian, for example, a transgenic chicken, which contains a transgene encoding the fusion protein molecules. In one embodiment, the fusion protein molecules (e.g., Fc fusion protein molecules) such as CTLA4-Fc molecules are produced in an avian oviduct cell, for example, a tubular gland cell. In one embodiment, the fusion protein molecules (e.g., Fc fusion protein molecules) such as CTLA4-Fc molecules are contained in a hard shell egg, for example, a hard shell egg laid by an avian, for example, a chicken, which contains a transgene encoding the fusion protein molecules. For example, the fusion protein molecules may be present in the contents of an intact hard shell egg (e.g., in the egg white). In one particularly useful embodiment, the fusion protein molecules of the invention are CTLA4-Fc.

In one aspect, the invention is drawn to compositions containing fusion protein molecules (e.g., Fc fusion protein molecules) such as CTLA4-Fc molecules produced in an avian (e.g., a transgenic chicken) which contains a transgene encoding the fusion protein molecules. In one embodiment, the fusion protein molecules in the composition are produced in an oviduct cell (e.g., a tubular gland cell) of a transgenic avian (e.g., transgenic chicken) and the molecules are isolated from egg white produced by the transgenic avian.

It is contemplated that the fusion protein molecules (e.g., Fc fusion protein molecules) such as CTLA4-Fc molecules in a composition of the invention are N-glycosylated and/or O-glycosylated. In one embodiment, the fusion protein molecules (e.g., Fc fusion protein molecules) such as CTLA4-Fc molecules in the composition are N-glycosylated and/or O-glycosylated in the oviduct cell (e.g., tubular gland cell) of the bird, for example, a chicken.

In one aspect, the invention relates to a composition, for example, a pharmaceutical composition, containing isolated fusion protein molecules (e.g., Fc fusion protein molecules) such as CTLA4-Fc molecules having an avian derived glycosylation pattern. In one aspect, the invention relates to a composition, for example, a pharmaceutical composition, containing isolated fusion protein molecules (e.g., Fc fusion protein molecules) such as CTLA4-Fc molecules, having a poultry derived glycosylation pattern. In one aspect, the invention relates to a composition, for example, a pharmaceutical composition, containing isolated and glycosylated fusion protein molecules (e.g., Fc fusion protein molecules) such as CTLA4-Fc molecules, produced in accordance with the invention.

In one embodiment, fusion protein molecules (e.g., Fc fusion protein molecules) such as CTLA4-Fc molecules in compositions of the invention contain a glycosylation pattern other than that of fusion protein molecules (e.g., Fc fusion protein molecules) such as CTLA4-Fc molecules produced in a mammalian cell. In one embodiment, fusion protein molecules (e.g., Fc fusion protein molecules) such as CTLA4-Fc molecules in compositions of the invention contain a glycosylation pattern other than that of fusion protein molecules (e.g., Fc fusion protein molecules) such as CTLA4-Fc molecules produced in a CHO cell.

In one embodiment, fusion protein molecules (e.g., Fc fusion protein molecules) such as CTLA4-Fc molecules of the invention are attached to one or more N-linked oligosaccharide structures disclosed herein (e.g., those shown in Example 5). In one embodiment, fusion protein molecules (e.g., Fc fusion protein molecules) such as CTLA4-Fc molecules of the invention are attached to one or more O-linked oligosaccharide structures disclosed in US patent publication No. 2009/0074718, published Mar. 19, 2009, the disclosure of which is incorporated in its entirety herein by reference.

One aspect of the present invention relates to avian hard shell eggs (e.g., chicken hard shell eggs) which contain a fusion protein including, but not limited to, a pharmaceutical fusion protein. The fusion protein in the egg is encoded by a transgene of a transgenic avian. The fusion protein may be present in an egg laid by the avian in any useful amount. In one embodiment, the fusion protein of the invention is present in an amount in a range of between about 0.01 µg per hard-shell egg and about 1 gram per hard-shell egg. In another embodiment, the fusion protein is present in an amount in a range of between about 1 µg per hard-shell egg and about 1 gram per hard-shell egg. For example, the fusion protein may be present in an amount in a range of between about 10 µg is per hard-shell egg and about 1 gram per hard-shell egg (e.g., a range of between about 10 µg per hard-shell egg and about 400 mg per hard-shell egg).

In one embodiment, the fusion protein of the invention, for example, the pharmaceutical fusion protein (e.g., an Fc fusion protein) is present in the egg white of the egg. In one embodiment, the fusion protein is present in an amount in a range of between about 1 ng per ml of egg white and about 0.2 gram per ml of egg white. For example, the fusion protein may be present in an amount in a range of between about 0.1 µg per ml of egg white and about 0.2 gram per ml of egg white (e.g., the fusion protein may be present in an amount in a range of between about 1 µg per ml of egg white and about 100 mg per ml of egg white. In one embodiment, the fusion protein is present in an amount in a range of between about 1 µg per ml of egg white and about 50 mg per ml of egg white. For example, the fusion protein may be present in an amount in a range of between about 1 µg per ml of egg white and about 10 mg per ml of egg white (e.g., the fusion protein may be present in an amount in a range of between about 1 µg per ml of egg white and about 1 mg per ml of egg white). In one embodiment, the fusion protein is present in an amount of more than 0.1 µg per ml of egg white. In one embodiment, the fusion protein is present in an amount of more than 0.5 µg is per ml of egg white. In one embodiment, the fusion protein is present in an amount of more than 1 µg per ml of egg white. In one embodiment, the fusion protein is present in an amount of more than 1.5 µg per ml of egg white.

In one embodiment, the invention provides for the production of hard shell eggs containing a glycosylated Fc fusion protein. For example, the eggs may contain a CTLA4-Fc fusion protein in accordance with the invention.

In one embodiment, the invention includes Fc fusion proteins wherein the Fc portion of the protein contains a single glycosylation site which is glycosyated with an oligosaccharide which contains no sialic acid. In one embodiment, the invention includes Fc fusion proteins wherein the Fc portion contains a single glycosylation site which is glycosylated with an oligosaccharide which is terminated exclusively with N-acetylglucosamine.

The avians developed from the blastodermal cells into which a vector containing a transgene encoding a fusion protein of the invention has been introduced are the G0 generation and can be referred to as "founders". Founder birds are typically chimeric for each inserted transgene. That is, only some of the cells of the G0 transgenic bird contain the transgene(s). The G0 generation typically is also hemizygous for the transgene(s). The G0 generation may be bred to non-transgenic animals to give rise to G1 transgenic offspring which are also hemizygous for the transgene and contain the transgene(s) in essentially all of the bird's cells. The G1 hemizygous offspring may be bred to non-transgenic animals giving rise to G2 hemizygous offspring or may be bred together to give rise to G2 offspring homozygous for the transgene. Substantially all of the cells of birds which are positive for the transgene that are derived from G1 offspring will contain the transgene(s). In one embodiment, hemizygotic G2 offspring from the same line can be bred to produce G3 offspring homozygous for the transgene. In one embodiment, hemizygous G0 animals are bred together to give rise to homozygous G1 offspring containing two copies of the transgene(s) in each cell of the animal. These are merely examples of certain useful breeding methods and the present invention contemplates the employment of any useful breeding method such as those known to individuals of ordinary skill in the art.

The invention also includes, methods of making glycosylated proteins disclosed herein including fusion proteins (e.g., Fc fusion proteins) such as CTLA4-Fc by any useful method including, but not limited to, producing a transgenic avian which contains a transgene encoding the fusion protein wherein the fusion protein is produced in an oviduct cell, for example, a tubular gland cell. The method can also include isolating the protein. Also included are the eggs laid by the avians which contain the protein, for example, the fusion protein (e.g., Fc fusion proteins) such as CTLA4-Fc.

The invention also provides for compositions which contain isolated mixtures of an individual type of useful protein molecule, such as those proteins disclosed herein, where one or more of the protein molecules contained in the mixture has a specific oligosaccharide structure attached, in particular, an oligosaccharide structure disclosed herein which may be produced by a transgenic avian. For example, the invention provides for isolated mixtures of Fc fusion protein molecules, for example, CTLA4-Fc molecules (e.g., CTLA4-Fc of SEQ ID NO: 2) glycosylated with one or more of N-1, N-2, N-3, N-4, N-5, N-6, N-7 and/or N-8 of Example 5. It is also contemplated that the fusion protein molecules (e.g., Fc fusion protein molecules) such as CTLA4-Fc molecules of the invention may be N-glycosylated with one or more of the N-linked oligosaccharide molecules which are shown in US patent publication No. 2009/0074718, published Mar. 19, 2009, the disclosure of which is incorporated in its entirety herein by reference.

Any useful combination of features described herein is included within the scope of the present invention provided that the features included in any such combination are not mutually inconsistent as will be apparent from the context, this specification, and the knowledge of one of ordinary skill in the art.

Additional objects and aspects of the present invention will become more apparent upon review of the detailed description set forth below when taken in conjunction with the accompanying figures, which are briefly described as follows.

BRIEF DESCRIPTION OF THE DRAWINGS

FIG. 1 (SEQ ID NO: 1) shows the amino acid sequence of an Fc portion of particular Fc fusion proteins of the invention. The predicted glycosylation site is shown underlined and in bold.

FIG. 2 (SEQ ID NO: 2) shows the amino acid sequence of CTLA4-Fc produced in accordance with the invention. Three predicted glycosylation sites are underlined and in bold in FIG. 2.

FIG. 5A (SEQ ID NO: 5) shows an amino acid sequence for lysosomal acid lipase and FIG. 5B (SEQ ID NO: 6) shows an amino acid sequence for glucocerebrosidase.

DETAILED DESCRIPTION

Figure 3:
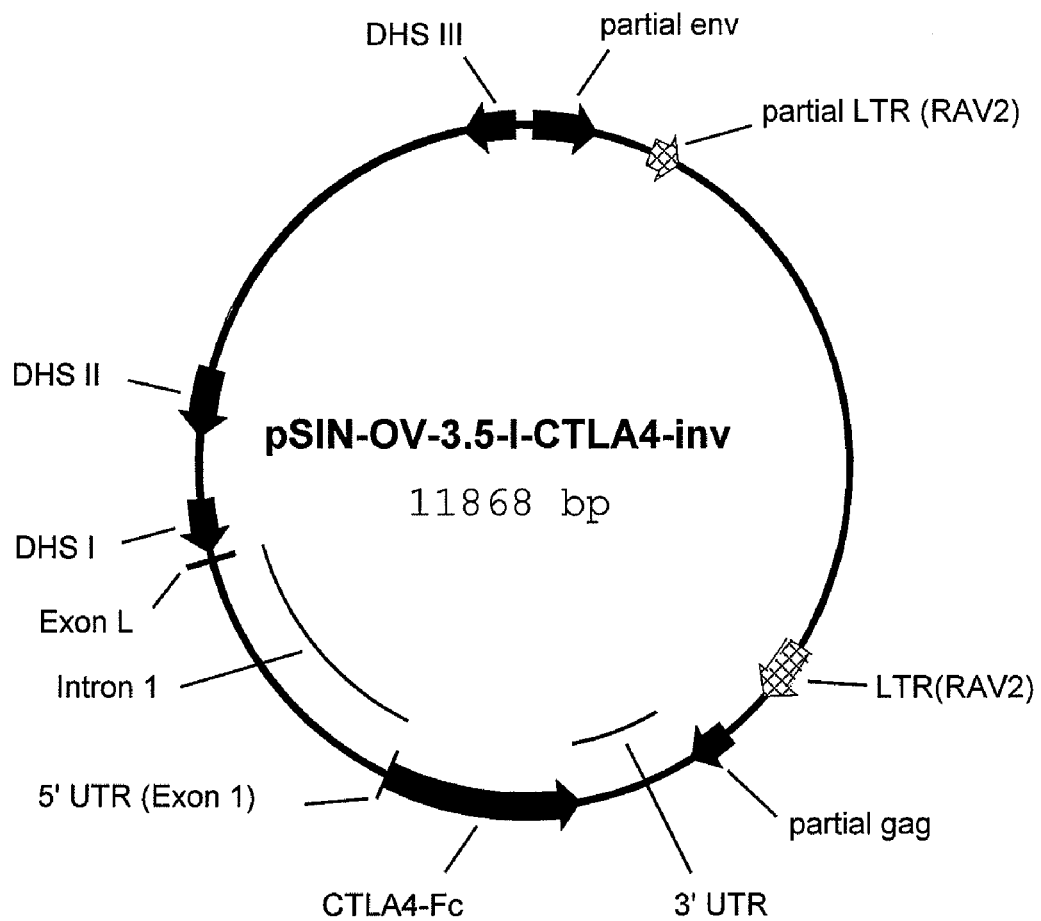
FIG. 3 shows a circular map of the pSIN-OV-3.5-I-CTLA4-inv vector. The nucleotide sequence of pSIN-OV-3.5-I-CTLA4-inv is shown in SEQ ID NO: 3.

Certain definitions are set forth herein to illustrate and define the meaning and scope of the various terms used to describe the invention herein.

A "nucleic acid or polynucleotide sequence" includes, but is not limited to, eukaryotic mRNA, cDNA, genomic DNA, and synthetic DNA and RNA sequences, comprising the natural nucleoside bases adenine, guanine, cytosine, thymidine, and uracil. The term also encompasses sequences having one or more modified bases.

The term "avian" as used herein refers to any species, subspecies or race of organism of the taxonomic class ava, such as, but not limited to chickens, quails, turkeys, ducks, geese, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Australorp, Minorca, Amrox, California Gray), as well as strains of turkeys, pheasants, quails, ducks, ostriches and other poultry commonly bred in commercial quantities. It also includes an individual avian organism in all stages of development, including embryonic and fetal stages.

A "fusion protein" is a protein comprising two or more separate proteins/peptides with functional properties derived from each of the original two or more proteins/peptides.

"Fc fusion protein" is a protein comprising a functional Fc portion of an antibody such as human immunoglobulin G1 (IgG1) linked to a second protein or protein portion. The linkage may be through a hinge domain or other linkage region.

"CTLA4-Fc" is a fusion protein that consists of the extracellular domain of human cytotoxic T-lymphocyte-associated antigen 4 (CTLA-4) linked to a modified Fc (hinge, CH2, and CH3 domains) portion of human immunoglobulin G1 (IgG1).

"Therapeutic proteins" or "pharmaceutical proteins" include an amino acid sequence which in whole or in part makes up a drug.

A "coding sequence" or "open reading frame" refers to a polynucleotide or nucleic acid sequence which can be transcribed and translated (in the case of DNA) or translated (in the case of mRNA) into a polypeptide in vitro or in vivo when placed under the control of appropriate regulatory sequences. The boundaries of the coding sequence are determined by a translation start codon at the 5' (amino) terminus and a translation stop codon at the 3' (carboxy) terminus. A transcription termination sequence will usually be located 3' to the coding sequence. A coding sequence may be flanked on the 5' and/or 3' ends by untranslated regions.

Nucleic acid "control sequences" or "regulatory sequences" refer to promoter sequences, translational start and stop codons, ribosome binding sites, polyadenylation signals, transcription termination sequences, upstream regulatory domains, enhancers, and the like, as necessary and sufficient for the transcription and translation of a given coding sequence in a defined host cell. Examples of control sequences suitable for eukaryotic cells are promoters, polyadenylation signals, and enhancers. All of these control sequences need not be present in a recombinant vector so long as those necessary and sufficient for the transcription and translation of the desired coding sequence are present.

"Operably or operatively linked" refers to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "heterologous" and "exogenous" as they relate to nucleic acid sequences such as coding sequences and control sequences, denote sequences that are not normally associated with a region of a recombinant construct or with a particular chromosomal locus, and/or are not normally associated with a particular cell. Thus, an "exogenous" region of a nucleic acid construct is an identifiable segment of nucleic acid within or attached to another nucleic acid molecule that is not found in association with the other molecule in nature. For example, an exogenous region of a construct could include a coding sequence flanked by sequences not found in association with the coding sequence in nature. Another example of an exogenous coding sequence is a construct where the coding sequence itself is not found in nature (e.g., synthetic sequences having codons different from the native gene). Similarly, a host cell transformed with a construct or nucleic acid which is not normally present in the host cell would be considered exogenous to the cell.

As used herein the terms "oligosaccharide", "oligosaccharide pattern", "oligosaccharide structure", "carbohydrate chain", "glycosylation pattern" and "glycosylation structure" can have essentially the same meaning and refer to one or more structures which are formed from sugar residues and are attached to proteins of the invention.

"Exogenous protein" as used herein refers to a protein not naturally present in a particular tissue or cell and is the expression product of an exogenous expression construct or transgene, and/or a protein not naturally present in a given quantity in a particular tissue or cell. A protein that is exogenous to an egg is a protein that is not normally found in the egg. For example, a protein exogenous to an egg may be a protein that is present in the egg as a result of the expression of an exogenous or heterologous coding sequence present in a transgene of the animal laying the egg.

"Endogenous nucleotide sequence" refers to a naturally occurring nucleotide sequence or fragment thereof normally associated with a particular cell.

The expression products described herein may consist of proteinaceous material having a defined chemical structure. However, the precise structure depends on a number of factors, particularly chemical modifications common to proteins. For example, since all proteins contain ionizable amino and carboxyl groups, the protein may be obtained in acidic or basic salt form, or in neutral form. The primary amino acid sequence may be derivatized using sugar molecules (glycosylation) or by other chemical derivatizations involving covalent or ionic attachment with, for example, lipids, phosphate, acetyl groups and the like, often occurring through association with saccharides. These modifications may occur in vitro or in vivo, the latter being performed by a host cell through post-translational processing systems. Such modifications may increase or decrease the biological activity of the molecule, and such chemically modified molecules are also intended to come within the scope of the invention.

Various methods of cloning, amplification, expression, and purification will be apparent to the skilled artisan. Representative methods are disclosed in Sambrook, Fritsch, and Maniatis, Molecular Cloning, a Laboratory Manual, 2nd Ed., Cold Spring Harbor Laboratory (1989).

"Vector" means a polynucleotide comprised of single strand, double strand, circular, or supercoiled DNA or RNA. A typical vector may be comprised of one or more the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. The nucleic acid cassette can include a restriction site for insertion of the nucleic acid sequence to be expressed. In a functional vector the nucleic acid cassette typically contains the nucleic acid sequence to be expressed including translation, initiation and termination sites. An intron optionally may be included in the construct, for example, 5' to the coding sequence. A vector is constructed so that the particular coding sequence is located in the vector with the appropriate regulatory sequences, the positioning and orientation of the coding sequence with respect to the control sequences being such that the coding sequence is transcribed under the "control" of the control sequences or regulatory sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. In one embodiment, the coding sequence is cloned directly into an expression vector which already contains the control sequences and an appropriate restriction site which is in reading frame with and under regulatory control of the control sequences.

A "promoter" is a site on the DNA to which RNA polymerase binds to initiate transcription of a gene. In some embodiments the promoter will be modified by the addition or deletion of sequences, or replaced with alternative sequences, including natural and synthetic sequences as well as sequences which may be a combination of synthetic and natural sequences. Many eukaryotic promoters contain two types of recognition sequences: the TATA box and the upstream promoter elements. The former, located upstream of the transcription initiation site, is involved in directing RNA polymerase to initiate transcription at the correct site, while the latter appears to determine the rate of transcription and is upstream of the TATA box. Enhancer elements can also stimulate transcription from linked promoters, but many function exclusively in a particular cell type. Many enhancer/promoter elements derived from viruses, e.g., the SV40 promoter, the cytomegalovirus (CMV) promoter, the rous-sarcoma virus (RSV) promoter, and the murine leukemia virus (MLV) promoter are all active in a wide array of cell types, and are termed "ubiquitous". In one embodiment, non-constitutive promoters such as the mouse mammary tumor virus (MMTV) promoter are used in the present invention. The nucleic acid sequence inserted in the cloning site may have any open reading frame encoding a polypeptide of interest, with the proviso that where the coding sequence encodes a polypeptide of interest, it should preferably lack cryptic splice sites which can block production of appropriate mRNA molecules and/or produce aberrantly spliced or abnormal mRNA molecules.

The term "poultry derived" refers to a composition or substance produced by or obtained from poultry. "Poultry" refers to birds that can be kept as livestock, including but not limited to, chickens, duck, turkey, quail and ratites. For example, "poultry derived" may refer to chicken derived, turkey derived and/or quail derived.

A "retroviral particle", "transducing particle", or "transduction particle" refers to a replication-defective or replication-competent virus capable of transducing non-viral DNA or RNA into a cell.

The terms "transformation", "transduction" and "transfection" all denote the introduction of a polynucleotide into a cell such as an avian cell.

"Magnum" is that part of the oviduct between the infundibulum and the isthmus containing tubular gland cells that synthesize and secrete the egg white proteins of the egg.

The term "optimized" is used in the context of "avian oviduct optimized coding sequence", wherein the most frequently used codons for each particular amino acid found in the egg white proteins ovalbumin, lysozyme, ovomucoid, and ovotransferrin are used in the design of the avian oviduct optimized proteins of the invention. More specifically, the DNA sequence for optimized protein is based on the hen oviduct optimized codon usage and is created using the BACKTRANSLATE program of the Wisconsin Package, Version 9.1 (Genetics Computer Group Inc., Madison, Wis.) with a codon usage table compiled from the chicken (*Gallus gallus*) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU is used as the codon for the majority of alanines in the avian oviduct optimized protein coding sequence.

The invention includes fusion proteins (e.g., Fc fusion proteins) such as CTLA4-Fc having N-linked glycosylation structures at three sites wherein the structures at each of the three sites are selected from one of N-1, N-2, N-3, N-4, N-5, N-6, N-7 and N-8 of Example 5.

The invention includes fusion proteins (e.g., Fc fusion proteins) such as CTLA4-Fc having an N-linked glycosylation structure at an Fc N-linked glycosylation site wherein the structure is selected from one of N-1, N-2, N-3, N-4, N-5, N-6, N-7 and N-8 of Example 5.

The invention also includes a mixture of fusion protein molecules (e.g., Fc fusion protein molecules) such as CTLA4-Fc molecules wherein some or all of the fusion protein molecules have one or more glycosylation structures selected from Structures N-1, N-2, N-3, N-4, N-5, N-6, N-7 and N-8 of Example 5. In one embodiment, the mixture of fusion protein molecules (e.g., Fc fusion protein molecules) such as CTLA4-Fc molecules is purified or isolated, for example, isolated from an egg or purified or isolated from egg white.

The invention also includes an individual fusion protein molecule (e.g., Fc fusion protein molecule) such as a CTLA4-Fc molecule comprising a Structure N-1. The invention also includes an individual fusion protein molecule (e.g., Fc fusion protein molecule) such as a CTLA4-Fc molecule comprising a Structure N-2. The invention also includes an individual fusion protein molecule (e.g., Fc fusion protein molecule) such as a CTLA4-Fc molecule comprising a Structure N-3. The invention also includes an individual fusion protein molecule (e.g., Fc fusion protein molecule) such as a CTLA4-Fc molecule comprising a Structure N-4. The invention also includes an individual fusion protein molecule (e.g., Fc fusion protein molecule) such as a CTLA4-Fc molecule comprising a Structure N-5. The invention also includes an individual fusion protein molecule (e.g., Fc fusion protein molecule) such as a CTLA4-Fc molecule comprising a Structure N-6. The invention also includes an individual fusion protein molecule (e.g., Fc fusion protein molecule) such as a CTLA4-Fc molecule comprising a Structure N-7. The invention also includes an individual fusion protein molecule (e.g., Fc fusion protein molecule) such as a CTLA4-Fc molecule comprising a Structure N-8. In one embodiment, the individual fusion protein molecule (e.g., Fc fusion protein molecule) such as a CTLA4-Fc molecule is present in a mixture of fusion protein molecules (e.g., Fc fusion protein molecules) such as CTLA4-Fc molecules which has been produced in a transgenic avian, e.g., a transgenic chicken. In one embodiment, the individual fusion protein molecule (e.g., Fc fusion protein molecule) such as a CTLA4-Fc molecule is present in a mixture of fusion protein molecules (e.g., Fc fusion protein molecules) such as CTLA4-Fc molecules which has been isolated or purified, for example, the mixture is isolated or purified from an egg or from egg white produced by a transgenic avian. In one embodiment, the individual fusion protein molecule (e.g., Fc fusion protein molecule) such as a CTLA4-Fc molecule is isolated or purified. The individual fusion protein molecules may be part of a composition of the invention. The mixtures of fusion protein molecules may be part of a composition of the invention. The invention also includes egg white containing the mixtures of fusion protein molecules of the invention.

The invention includes CTLA4-Fc molecule as shown in FIG. 2 where each of the Asn-102, Asn-134 and Asn-233 glycosylation sites are glycosylated with one of the N-1, N-2, N-3, N-4, N-5, N-6, N-7, N-8 structures of Example 5.

The invention includes Fc fusion proteins molecules where the Asn-102 glycosylation site of the Fc portion shown in FIG. 1 is glycosylated with one of the N-1, N-2, N-3, N-4, N-5, N-6, N-7, N-8 Structures.

In one aspect, the invention includes fusion proteins (e.g., Fc fusion proteins) such as CTLA4-Fc wherein the fusion proteins have a poultry derived glycosylation pattern such as a chicken or quail derived glycosylation pattern. In one aspect, the invention includes fusion proteins (e.g., Fc fusion proteins) such as CTLA4-Fc wherein the fusion proteins have a transgenic avian derived glycosylation pattern.

In one embodiment, the glycosylation pattern is other than that of the same fusion protein produced in a CHO cell. For example, the compositions can include a fusion protein (e.g., Fc fusion protein) such as CTLA4-Fc with a poultry or avian derived carbohydrate chain (i.e., glycosylation structure) and that carbohydrate chain or glycosylation structure is not found on that fusion protein obtained from CHO cell production. However, the composition may also include a fusion protein (e.g., Fc fusion protein) such as CTLA4-Fc that has one or more glycosylation structures that are the same as that found on the fusion protein when produced in CHO cells. That is, the mixture of fusion protein molecules (e.g., Fc fusion protein molecules) such as CTLA4-Fc molecules may contain one or more fusion protein molecules having an oligosaccharide pattern disclosed herein and one or more of the fusion protein molecules in the mixture may have an oligosaccharide pattern which could also be obtained in CHO cell production.

In one embodiment, the glycosylation pattern of a fusion protein (e.g., Fc fusion protein) such as CTLA4-Fc produced in accordance with the invention is other than that of the fusion protein produced in mammalian cells. For example, the compositions can include a fusion protein (e.g., Fc fusion protein) such as CTLA4-Fc molecule with a poultry or avian derived carbohydrate chain (i.e., glycosylation structure) and that carbohydrate chain or glycosylation structure is not found on that fusion protein obtained from mammalian cells. However, the composition may also include a fusion protein (e.g., Fc fusion protein) such as CTLA4-Fc that has one or more glycosylation structures that are the same as that found on the fusion protein produced in mammalian cells. That is, the mixture of fusion protein molecules (e.g., Fc fusion protein molecules) such as CTLA4-Fc molecules may contain one or more fusion protein molecules having an oligosaccharide pattern disclosed herein and one or more of the fusion protein molecules in the mixture may have an oligosaccharide pattern which could also be obtained in mammalian cell production.

In one embodiment, provided for are fusion proteins of the invention (e.g., Fc fusion proteins) such as CTLA4-Fc which are isolated. In one embodiment, the fusion proteins (e.g., Fc fusion proteins) such as CTLA4-Fc contained in a composition are isolated. For example, the fusion proteins (e.g., Fc fusion proteins) such as CTLA4-Fc may be isolated from egg white. The isolated fusion proteins may be fusion protein molecules that do not all have the same glycosylation structures among the fusion protein molecules or the isolated fusion protein may be an isolated individual species of fusion protein molecules having only one particular glycosylation structure at a particular glycosylation site among the species of fusion protein molecules.

In one embodiment, about 95% or more of the N-linked oligosaccharides present on the fusion protein molecules (e.g., Fc fusion protein molecules) such as CTLA4-Fc molecules of the invention do not contain sialic acid. In another embodiment, about 90% or more of the N-linked oligosaccharides present on the fusion proteins (e.g., Fc-fusion proteins) such as CTLA4-Fc of the invention do not contain sialic acid. In another embodiment, about 80% or more of the N-linked oligosaccharides present on the fusion protein molecules (e.g., Fc fusion protein molecules) such as CTLA4-Fc molecules of the invention do not contain sialic acid. In another embodiment, more than about 70% or more of the N-linked oligosaccharides present on the fusion protein molecules (e.g., Fc fusion protein molecules) such as CTLA4-Fc molecules of the invention do not contain sialic acid. In another embodiment, about 60% or more of the N-linked oligosaccharides present on the fusion protein molecules (e.g., Fc fusion protein molecules) such as CTLA4-Fc molecules of the invention do not contain sialic acid. In another embodiment, about 50% or more of the N-linked oligosaccharides present on the fusion protein molecules (e.g., Fc fusion protein molecules) such as CTLA4-Fc molecules of the invention do not contain sialic acid.

In one embodiment, the oligosaccharides present on the fusion protein molecules (e.g., Fc fusion protein molecules) such as CTLA4-Fc molecules of the invention do not contain fucose. In another embodiment, about 90% or more of the N-linked oligosaccharides present on the fusion protein molecules (e.g., Fc fusion protein molecules) such as CTLA4-Fc molecules of the invention do not contain fucose. In another embodiment, about 80% or more of the N-linked oligosaccharides present on the fusion protein molecules (e.g., Fc fusion protein molecules) such as CTLA4-Fc molecules of the invention do not contain fucose. In another embodiment, about 70% or more of the N-linked oligosaccharides present on the fusion protein molecules (e.g., Fc fusion protein molecules) such as CTLA4-Fc molecules of the invention do not contain fucose. In another embodiment, about 60% or more of the N-linked oligosaccharides present on the fusion protein molecules (e.g., Fc fusion protein molecules) such as CTLA4-Fc molecules of the invention do not contain fucose. In another embodiment, about 50% or more of the N-linked oligosaccharides present on the fusion protein molecules (e.g., Fc fusion protein molecules) such as CTLA4-Fc molecules of the invention do not contain fucose. In one embodiment, the percentages in this paragraph refer specifically to the percentage of N-linked oligosaccharide structure present only on the Fc portion of Fc fusion protein molecules such as CTLA4-Fc molecules of the invention that do not contain fucose.

In one embodiment, about 95% or more of the N-linked oligosaccharides present on the fusion protein molecules (e.g., Fc fusion protein molecules) such as CTLA4-Fc molecules of the invention are terminated partially or exclusively with N-acetyl glucosamine. In another embodiment, about 90% or more of the N-linked oligosaccharides present on the fusion protein molecules (e.g., Fc fusion protein molecules) such as CTLA4-Fc molecules of the invention are terminated partially or exclusively with N-acetyl glucosamine. In another embodiment, about 80% or more of the N-linked oligosaccharides present on the fusion protein molecules (e.g., Fc fusion protein molecules) such as CTLA4-Fc molecules of the invention are terminated partially or exclusively with N-acetyl glucosamine. In another embodiment, about 70% or more of the N-linked oligosaccharides present on the fusion protein molecules (e.g., Fc fusion protein molecules) such as CTLA4-Fc molecules of the invention are terminated partially or exclusively with N-acetyl glucosamine. In another embodiment, about 60% or more of the N-linked oligosaccharides present on the fusion protein molecules (e.g., Fc fusion protein molecules) such as CTLA4-Fc molecules of the invention are terminated partially or exclusively with N-acetyl glucosamine. In another embodiment, about 50% or more of the N-linked oligosaccharides present on the fusion protein molecules (e.g., Fc fusion protein molecules) such as CTLA4-Fc molecules of the invention are terminated partially or exclusively with N-acetyl glucosamine.

In one embodiment, none or essentially none of the N-linked oligosaccharide structure types present on the fusion protein molecules (e.g., Fc fusion protein molecules) such as CTLA4-Fc molecules of the invention contain sialic acid. In another embodiment, about 95% or more of the N-linked oligosaccharide structure types present on the fusion protein molecules (e.g., Fc fusion protein molecules) such as CTLA4-Fc molecules of the invention do not contain sialic acid. In another embodiment, about 90% or more of the N-linked oligosaccharide structure types present on the molecules of the invention do not contain sialic acid. In another embodiment, about 80% or more of the N-linked oligosaccharide structure types present on the molecules of the invention do not contain sialic acid. In another embodiment, about 70% or more of the N-linked oligosaccharide structure types present on the molecules of the invention do not contain sialic acid. In another embodiment, about 60% or more of the N-linked oligosaccharide structure types present on the molecules of the invention do not contain sialic acid.

In one embodiment, all of the N-linked oligosaccharides structure types present on the fusion protein molecules (e.g., Fc fusion protein molecules) such as CTLA4-Fc molecules of the invention are terminated partially or exclusively with N-acetyl glucosamine. In another embodiment, about 95% or more of the N-linked oligosaccharide structure types present on the fusion protein molecules (e.g., Fc fusion protein molecules) such as CTLA4-Fc molecules of the invention are terminated partially or exclusively with N-acetyl glucosamine. In another embodiment, about 90% or more of the N-linked oligosaccharide structure types present on the fusion protein molecules (e.g., Fc fusion protein molecules) such as CTLA4-Fc molecules of the invention are terminated partially or exclusively with N-acetyl glucosamine. In another embodiment, about 80% or more of the N-linked oligosaccharide structure types present on the fusion protein molecules (e.g., Fc fusion protein molecules) such as CTLA4-Fc molecules of the invention are terminated partially or exclusively with N-acetyl glucosamine. In another embodiment, about 70% or more of the N-linked oligosaccharide structure types present on the fusion protein molecules (e.g., Fc fusion protein molecules) such as CTLA4-Fc molecules of the invention are terminated partially or exclusively with N-acetyl glucosamine. In another embodiment, about 60% or more of the N-linked oligosaccharide structure types present on the fusion protein molecules (e.g., Fc fusion protein molecules) such as CTLA4-Fc molecules of the invention are terminated partially or exclusively with N-acetyl glucosamine. In another embodiment, about 50% or more of the N-linked oligosaccharide structure types present on the fusion protein molecules (e.g., Fc fusion protein molecules) such as CTLA4-Fc molecules of the invention are terminated partially or exclusively with N-acetyl glucosamine.

In one embodiment, essentially none of the N-linked oligosaccharide structure types present on the fusion protein molecules (e.g., Fc fusion protein molecules) such as CTLA4-Fc molecules of the invention contain fucose. In another embodiment, about 95% or more of the N-linked oligosaccharide structure types present on the fusion protein molecules (e.g., Fc fusion protein molecules) such as CTLA4-Fc molecules of the invention do not contain fucose. In another embodiment, about 90% or more of the N-linked oligosaccharide structure types present on the fusion protein molecules (e.g., Fc fusion protein molecules) such as CTLA4-Fc molecules of the invention do not contain fucose. In another embodiment, about 80% or more of the N-linked oligosaccharide structure types present on the fusion protein molecules (e.g., Fc fusion protein molecules) such as CTLA4-Fc molecules of the invention do not contain fucose. In another embodiment, about 70% or more of the N-linked oligosaccharide structure types present on the fusion protein molecules (e.g., Fc fusion protein molecules) such as CTLA4-Fc molecules of the invention do not contain fucose. In another embodiment, about 60% or more of the N-linked oligosaccharide structure types present on the fusion protein molecules (e.g., Fc fusion protein molecules) such as CTLA4-Fc molecules of the invention do not contain fucose. In one embodiment, the percentages in this paragraph refer specifically to the percentage of N-linked oligosaccharide structure types present only on the Fc portion of Fc fusion protein molecules such as CTLA4-Fc molecules of the invention that do not contain fucose.

Each of the glycosylation structures shown in Example 5 (i.e., N-1 to N-8) is an "oligosaccharide structure type".

In one embodiment, the fusion protein (e.g., Fc fusion protein) such as CTLA4-Fc is present in a hard shell egg. For example, the fusion protein may be present in the egg white of a hard shell egg laid by a transgenic avian of the invention. That is, in one embodiment, the invention is directed to avian (e.g., chicken) egg white containing a fusion protein of the invention. In one embodiment, the fusion protein (e.g., Fc fusion protein) such as CTLA4-Fc is present in the egg white in an amount in excess of about 1 microgram per ml of egg white (e.g., present in an amount of about 1 microgram to about 0.5 gram per ml of egg white). For example, the fusion protein (e.g., Fc fusion protein) such as CTLA4-Fc can be present in an amount greater than about 2 micrograms per ml of egg white (e.g., present in an amount of about 2 micrograms to about 200 micrograms per ml of egg white).

N-linked oligosaccharides attached to CTLA4-Fc produced in transgenic chickens typically have little or no terminal sialic acid residues. This is in contrast to CTLA4-Fc produced in mammalian cells such as CHO cells where the N-linked oligosaccharide structures are extensively terminally sialylated. In addition, terminal N-Acetyl Glucosamine (NAcGlu) is present extensively on the N-linked oligosaccharide structures of the CTLA4-Fc produced in transgenic avians such as chickens which is not the case for CTLA4-Fc produced in mammalian cells such as CHO cells. Further, no fucose or only a small amount of fucose is present on the N-linked oligosaccharide structures of the CTLA4-Fc produced in transgenic avians such as chickens. However, fucose is thought to be present on all or most N-linked oligosaccharide structures of CTLA4-Fc (e.g., the Fc portion of an Fc fusion protein) produced in mammalian cells such as CHO cells.

It is understood that though the reported method of making compositions of the invention is in avians, the compositions are not limited thereto. For example, certain of the glycosylated protein molecules of the invention may be produced in other organisms such as transgenic fish, transgenic plants, such as tobacco and duck weed (*Lemna minor*).

The invention also contemplates that pegylating proteins produced as disclosed herein may be advantageous. See, for example, US patent publication No. 2007/0092486, published Apr. 26, 2007, the disclosure of which is incorporated it its entirety herein by reference.

While it is possible that, for use in therapy, therapeutic proteins produced in accordance with this invention may be administered in raw form, it is preferable to administer the therapeutic proteins as part of a pharmaceutical composition.

One aspect of the invention relates to compositions containing fusion protein molecules (e.g., Fc fusion protein molecules) such as CTLA4-Fc molecules produced in accordance with the invention. In a particularly useful embodiment, the fusion protein molecules (e.g., Fc fusion protein molecules) such as CTLA4-Fc molecules are purified or isolated. For example, the fusion protein molecules can be removed from the contents of a hard shell egg laid by a transgenic avian. In one embodiment, the fusion protein molecules (e.g., Fc fusion protein molecules) such as CTLA4-Fc molecules of the invention have a glycosylation pattern resulting from the molecules being produced in an oviduct cell of an avian.

Another aspect of the invention relates to compositions containing fusion protein molecules (e.g., Fc fusion protein molecules) such as CTLA4-Fc molecules produced in an avian oviduct cell (e.g., a tubular gland cell) that have a glycosylation pattern other than that of fusion protein molecules produced in a mammalian cell such as a CHO cell. In one aspect, the invention provides for compositions that contain isolated fusion protein molecules (e.g., Fc fusion protein molecules) such as CTLA4-Fc molecules having an avian or poultry derived glycosylation pattern. For example, the compositions can contain a mixture of fusion protein molecules (e.g., Fc fusion protein molecules) such as CTLA4-Fc molecules produced in avians, for example, chickens, in accordance with the invention and isolated from egg white. In one useful embodiment, the fusion protein molecules (e.g., Fc fusion protein molecules) such as CTLA4-Fc molecules are in pharmaceutical compositions.

The invention provides for pharmaceutical compositions comprising poultry or avian derived glycosylated fusion proteins (e.g., Fc fusion proteins) such as CTLA4-Fc, which may be pegylated, together with one or more pharmaceutically acceptable carriers thereof and, optionally, other therapeutic and/or prophylactic ingredients and methods of administering such pharmaceutical compositions. The carrier(s) must be "acceptable" in the sense of being compatible with the other ingredients of the formulation and not deleterious to the recipient thereof. Methods of treating a patient (e.g., quantity of pharmaceutical protein administered, frequency of administration and duration of treatment period) using pharmaceutical compositions of the invention can be determined using standard methodologies known to physicians of skill in the art.

Pharmaceutical compositions include those suitable for oral, rectal, nasal, topical (including buccal and sub-lingual), vaginal or parenteral. The pharmaceutical compositions include those suitable for administration by injection including intramuscular, sub-cutaneous and intravenous administration. The pharmaceutical compositions also include those for administration by inhalation or insufflation. The compositions or formulations may, where appropriate, be conveniently presented in discrete dosage units and may be prepared by any of the methods well known in the art of pharmacy. The methods of producing the pharmaceutical compositions typically include the step of bringing the therapeutic proteins into association with liquid carriers or finely divided solid carriers or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

Therapeutic proteins of the invention may also be formulated for parenteral administration (e.g., by injection, for example bolus injection or continuous infusion) and may be presented in unit dose form in ampoules, pre-filled syringes, small volume infusion or in multi-dose containers with an added preservative. The therapeutic proteins may be injected by, for example, subcutaneous injections, intramuscular injections, and intravenous infusions or injections.

The therapeutic proteins may take such forms as suspensions, solutions, or emulsions in oily or aqueous vehicles, and may contain formulatory agents such as suspending, stabilizing and/or dispersing agents. It is also contemplated that the therapeutic proteins may be in powder form, obtained by aseptic isolation of sterile solid or by lyophilization from solution, for constitution with a suitable vehicle, e.g., sterile, pyrogen-free water, before use.

For topical administration to the epidermis, the therapeutic proteins produced according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration wherein the carrier is a solid are most preferably represented as unit dose suppositories. Suitable carriers include cocoa butter and other materials commonly used in the art, and the suppositories may be conveniently formed by a mixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient, such carriers as are known in the art to be appropriate.

For intra-nasal administration the therapeutic proteins of the invention may be used as a liquid spray or dispersible powder or in the form of drops.

Drops may be formulated with an aqueous or non-aqueous base also comprising one or more dispersing agents, solubilizing agents or suspending agents. Liquid sprays are conveniently delivered from pressurized packs.

For administration by inhalation, therapeutic proteins according to the invention may be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

For administration by inhalation or insufflation, the therapeutic proteins according to the invention may take the form of a dry powder composition, for example a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient, may be employed.

The pharmaceutical compositions according to the invention may also contain other active ingredients such as antimicrobial agents, or preservatives.

In one embodiment, fusion proteins (e.g., Fc fusion proteins) such as CTLA4-Fc of the invention contained in pharmaceutical compositions are pegylated.

In a specific example, fusion protein molecules (e.g., Fc fusion protein molecules) such as CTLA4-Fc molecules produced as disclosed herein, and which may be pegylated, are employed in a pharmaceutical composition wherein each 1 mL contains 0.05 mg polysorbate 80, and is formulated at pH 6.2±0.2 with 2.12 mg sodium phosphate monobasic monohydrate, 0.66 mg sodium phosphate dibasic anhydrous, and 8.18 mg sodium chloride in water for injection. In another specific example, a fusion protein (e.g., Fc fusion protein) such as CTLA4-Fc produced as disclosed herein is employed in a pharmaceutical composition containing 7.5 mg/ml sodium chloride, 1.8 mg/ml sodium phosphate dibasic, 1.3 mg/ml sodium phosphate monobasic, 0.1 mg/ml edetate disodium dihydrate, 0.7 mg/ml Tween® 80 and 1.5 mg/ml m-cresol. In another specific example, a fusion protein (e.g., an Fc fusion protein) such as CTLA4-Fc produced as disclosed herein is employed in a pharmaceutical composition containing 0.82 mg/ml sodium acetate, 2.8 µl/ml glacial acetic acid, 50 mg/ml mannitol and 0.04 mg/ml Tween® 80.

In addition, it is contemplated that the therapeutic proteins of the invention may be used in combination with other therapeutic agents.

Compositions or compounds of the invention can be used to treat a variety of conditions. For example, there are many conditions for which treatment therapies are known to practitioners of skill in the art in which therapeutic proteins obtained from cell culture (e.g., CHO cells) are employed. The present invention contemplates that the glycosylated therapeutic proteins produced in an avian system can be employed to treat such conditions. That is, the invention contemplates the treatment of conditions known to be treatable by conventionally produced therapeutic proteins by using therapeutic proteins produced in accordance with the invention. For example, fusion proteins (e.g., Fc-fusion proteins) such as CTLA4-Fc produced in accordance with the invention can be used to treat human conditions such as rheumatoid arthritis, as understood in the art.

Generally, the dosage administered will vary depending upon known factors such as age, health and weight of the recipient, type of concurrent treatment, frequency of treatment, and the like. Usually, a dosage of active ingredient can be between about 0.0001 mg and about 10 mg per kilogram of body weight. Precise dosage, frequency of administration and time span of treatment can be determined by a physician skilled in the art of administration of the respective therapeutic protein.

By the methods of the present invention, transgenes can be introduced into avian embryonic blastodermal cells to produce a transgenic chicken, transgenic turkey, transgenic quail and other avian species, that carry a transgene in the genetic material of its germ-line tissue to produce proteins of the invention. The blastodermal cells are typically stage VII-XII cells, or the equivalent thereof, and in one embodiment are near stage X. The cells useful in the present invention include embryonic germ (EG) cells, embryonic stem (ES) cells & primordial germ cells (PGCs). The embryonic blastodermal cells may be isolated freshly, maintained in culture, or in a particularly useful embodiment, reside within an embryo.

Some vectors useful in carrying out the methods of the present invention are described herein. These vectors can be used for stable introduction of an exogenous coding sequence into the genome of an avian. The vectors may be used to produce proteins of the invention such as fusion proteins in specific tissues of an avian, for example, in the oviduct tissue of an avian. The vectors may also be used in methods to produce avian eggs which contain exogenous protein. In one embodiment, the coding sequence and the promoter are both positioned between 5' and 3' LTRs before introduction into blastodermal cells. In one embodiment, the vector is retroviral and the coding sequence and the promoter are both positioned between the 5' and 3' LTRs of the retroviral SIN vector. In one useful embodiment, the LTRs or retroviral vector is derived from the avian leukosis virus (ALV), murine leukemia virus (MLV), or lentivirus.

Useful retroviruses for introducing a transgene into the avian genome are the replication-deficient avian leucosis virus (ALV), the replication-deficient murine leukemia virus (MLV) and the lentivirus. Any of the vectors of the present invention may include a coding sequence encoding a signal peptide that will direct secretion of the protein expressed by the vector's coding sequence from the tubular gland cells of the oviduct. Where an exogenous protein would not otherwise be secreted, the vector containing the coding sequence is modified to comprise a DNA sequence encoding a useful signal peptide. The DNA sequence encoding the signal peptide is inserted in the vector such that it is located at the N-terminus of the protein encoded by the DNA. The signal peptide can direct secretion of the exogenous protein expressed by the vector into the egg white of a hard shell egg. The vector may include a marker gene, wherein the marker gene is operably linked to a promoter.

Any useful promoter can be employed. For example, the promoter can be a constitutive promoter such as a cytomegalovirus (CMV) promoter, a rous-sarcoma virus (RSV) promoter, a murine leukemia virus (MLV) promoter, a beta-actin promoter. The promoter can also be a magnum specific promoter such as an ovalbumin promoter, a lysozyme promoter, a conalbumin promoter, an ovomucoid promoter, an ovomucin promoter or an ovotransferrin promoter. Both constitutive and magnum specific promoters have proven suitable for expression of exogenous protein in the oviduct.

The methods of the invention which provide for the production of protein of the invention in the avian oviduct and the production of eggs which contain the exogenous protein involve an additional step subsequent to providing a suitable vector and introducing the vector into embryonic blastodermal cells so that the vector is integrated into the avian genome. The subsequent step involves deriving a mature transgenic avian from the transgenic blastodermal cells produced. Deriving a mature transgenic avian from the blastodermal cells typically involves transferring the vector into an embryo and allowing that embryo to develop fully, so that the transduced cells become incorporated into the avian as the embryo is allowed to develop. The resulting chick is then grown to maturity. In one embodiment, the cells of a blastodermal embryo are transfected or transduced with the vector directly within the embryo. The resulting embryo is allowed to develop and the chick allowed to mature.

The transgenic avian so produced from the transgenic blastodermal cells is known as a founder. Some founders will carry the transgene in the tubular gland cells in the magnum of their oviducts. These avians will express the exogenous protein encoded by the transgene in their oviducts. The exogenous protein may also be expressed in other tissues (e.g., blood) in addition to the oviduct. If the exogenous protein contains the appropriate signal sequence(s), it will be secreted into the lumen of the oviduct and into the egg white of the egg. Some founders are germ-line founders. A germ-line founder is a founder that carries the transgene in genetic material of its germ-line tissue, and may also carry the transgene in oviduct magnum tubular gland cells that express the exogenous protein. Therefore, in accordance with the invention, the transgenic avian will have tubular gland cells expressing the exogenous protein, and the offspring of the transgenic avian will also have oviduct magnum tubular gland cells that express the exogenous protein. In one embodiment of the invention, the transgenic avian is a chicken, a turkey or a quail.

Other specific examples of therapeutic proteins which may be produced as disclosed herein include, without limitation, factor VIII, b-domain deleted factor VIII, factor VIIa, factor IX, anticoagulants; hirudin, alteplase, tpa, reteplase, tpa, tpa—3 of 5 domains deleted, insulin, insulin lispro, insulin aspart, insulin glargine, long-acting insulin analogs, hgh, glucagons, tsh, follitropin-beta, fsh, gm-csf, pdgh, ifn alpha2, ifn alpha2a, ifn alpha2b, inf-apha, inf-beta 1b, ifn-beta 1a, ifn-gamma1b, il-2, il-11, hbsag, ospa, murine mab directed against t-lymphocyte antigen, murine mab directed against tag-72, tumor-associated glycoprotein, fab fragments derived from chimeric mab directed against platelet surface receptor gpII(b)/III(a), murine mab fragment directed against tumor-associated antigen ca125, murine mab fragment directed against human carcinoembryonic antigen, cea, murine mab fragment directed against human cardiac myosin, murine mab fragment directed against tumor surface antigen psma, murine mab fragments (fab/fab2 mix) directed against hmw-maa, murine mab fragment (fab) directed against carcinoma-associated antigen, mab fragments (fab) directed against nca 90, a surface granulocyte nonspecific cross reacting antigen, chimeric mab directed against cd20 antigen found on surface of b lymphocytes, humanized mab directed against the alpha chain of the il2 receptor, chimeric mab directed against the alpha chain of the il2 receptor, chimeric mab directed against tnf-alpha, humanized mab directed against an epitope on the surface of respiratory synctial virus, humanized mab directed against her 2, human epidermal growth factor receptor 2, human mab directed against cytokeratin tumor-associated antigen anti-ctla4, chimeric mab directed against cd 20 surface antigen of b lymphocytes dornase-alpha dnase, beta glucocerebrosidase, tnf-alpha, il-2-diptheria toxin fusion protein, tnfr-lgg fragment fusion protein laronidase, dnaases, alefacept, darbepoetin alfa (colony stimulating factor), tositumomab, murine mab, alemtuzumab, rasburicase, agalsidase beta, teriparatide, parathyroid hormone derivatives, adalimumab (lggl), anakinra, biological modifier, nesiritide, human b-type natriuretic peptide (hbnp), colony stimulating factors, pegvisomant, human growth hormone receptor antagonist, recombinant activated protein c, omalizumab, immunoglobulin e (lge) blocker, lbritumomab tiuxetan, ACTH, glucagon, somatostatin, somatotropin, thymosin, parathyroid hormone, pigmentary hormones, somatomedin, erythropoietin, luteinizing hormone, chorionic gonadotropin, hypothalmic releasing factors, etanercept, antidiuretic hormones, prolactin and thyroid stimulating hormone.

The invention also includes the production of lysosomal acid lipase (LAL) produced in accordance with the invention. The amino acid sequence for human LAL is well known in the art, see, for example, Anderson, R. A. and Sando, G. N., "Cloning and Expression of cDNA Encoding Human Lysosomal Acid Lipase/Cholesteryl Ester Hydrolase", Journal of Biological Chemistry, Vol. 266, No. 33, Issue of November 25, pp. 22479-22484 (1991). FIG. 5A shows an LAL sequence (mature protein 378 aa) which can be produced in accordance with the invention.

The invention also includes the production of glucocerebrosidase produced in accordance with the invention. Sequence information for human glucocerebrosidase is well known in the art, see, and, for example, Sorge, J., Wets, C., Westwood, B. and Beutler, E. "Molecular cloning and nucleotide sequence of human glucocerebrosidase cDNA", Proc. Natl. Acad. Sci, Vol 82, pp 7289-7293 (1985) and Tsuji, S., Choudary, P., Martin, B., Winfield, S., Barranger, J. and Grins, E., "Nucleotide Sequence of CDNA containing the complete coding sequence for Human Lysosomal Glucocerebrosidase". FIG. 5B shows a Glucocerebrosidase sequence (mature protein: 497 aa) which can be produced in accordance with the invention. A useful signal peptide is mefsspsreecpkplsrvsimagsltglllllqayswasg (39 aa).

Certain antibodies which may be produced in accordance with the invention include, without limitation, Muromonab; Satumomab pendetide; mAb=B72.3, conjugate of B72.3 and radioligand=CYT 103; Abciximab; Edrecolomab, Mab 17-1A; murine Mab fragment directed against tumor-associated antigen CA 125; Arcitumomab; Imciromab pentetate Capromab pendetide; murine Mab fragments (Fab/Fab2 mix) directed against HMW-MAA; Nofetumomab; Sulesomab; chimeric Mab directed against CD20 antigen found on surface of B lymphocytes; Daclizumab; Basiliximab; Palivizumab; Trastuzumab; human Mab directed against cytokeratin tumor-associated antigen; Rituximab; Infliximab; Gemtuzumab ozogamicin; Alemtuzumab; Tositumomab (conjugated to 131I); Omalizumab; Ibritumomab tiuxetan (conjugated to 90Y); Efalizumab; Cetuximab; Bevacizumab; Adalimumab (IgG1); Technetium (99 mTc) fanolesomab; Natalizumab; Ranibizumab; Panitumumab; Eculizumab.

In one particularly useful embodiment, antibodies produced in accordance with the invention are produced in a single chain form. See, for example, Lee et al, Molecular Immunology (1999) vol 36, p 61-71 which discloses the production of single chain antibodies, the disclosure of which is incorporated in its entirety herein by reference. For example, any antibody which can be produced in accordance with the invention in single chain form, including but not limited to each of the antibodies specifically disclosed herein, is contemplated for production in a single chain form in a transgenic avian oviduct.

Certain enzymes, such as human enzymes, which can be produced in accordance with the invention include Rasburicase; Asparaginase; Urokinase; Tenecteplase; adenosin deaminase; Glucocerebrosidase; lysosomal acid lipase (Cholestrase); Palmitoyl-protein thioesterase 1; PPT1, B-Galactosidase; Neuraminidase; heparan sulfamidase; N-acetyl-glucosaminidase; alpha-N-acetylglucosaminidase; alpha-glucosaminide N-acetyltransferase; N-acetylglucosamine-6-sulfate sulfatase; galactosylceramidase (GALC); Glucoronidase; NPC1; NPC2; Agalsidase alfa; Agalsidase beta; alpha-glucosidase; Acid Sphingomyelinase (ASM); N-acetylgalactosamine 6-sulfatase (GALNS or galactose 6-sulfatase); beta-galactosidase; Idursulfase; alpha-L-duronidase; Galsulfase: arylsulfatase B, BM 102, arylsulfatase B, N-acetylgalactosamine-4-sulfatase, ASB.; lysosomal alpha-mannosidase (LAMAN); beta-hexosaminidase; alglucosidase alfa; beta-hexosaminidase A; tripeptidyl peptidase 1 (TPP1).

Other protein therapeutics which can be produced in accordance with the invention include, without limitation, Factor VIII; B-domain deleted Factor VIII; Factor VIIa; Factor IX; anticoagulant; recombinant hirudin; anticoagulant; recombinant hirudin; Alteplase, tPA; Reteplase, human tPA—3 of 5 domains deleted; Factor XI; Factor XII (Hageman factor); Factor XIII; Alpha2-antiplasmin; Microplasmin; insulin lispro; Bio Lysprol, an insulin analog; insulin Aspart, insulin glargine, long-acting insulin analog; hGH; glucagons; TSH; follitropin-beta FSH; salmon calcitonin; (Teriparatide) Parathyroid hormone derivative; nesiritide, B-type natriuretic peptide (BNP); PDGH; Lutropin alfa; Choriogonadotropin alfa; Somatropin Pegvisomant, human growth hormone receptor antagonist; platelet derived growth factor (PDGF); Keratinocyte growth factor; fibroblast growth factor 23; insulin-like growth factor-1, IGF-1 complexed with IGFBP-3; HBsAg; vaccine containing HBsAgn as one component; OspA, a lipoprotein found on the surface of *B. burgorferi*; Hep B-IPV HIB vaccine; Hep B-IPV vaccine; Comb vaccine; Pneumococcal conjugate vaccine; Influenza virus vaccine live, intranasal; Alefacept, Immunosuppressive agent; TNF-alpha; TNFR-IgG fragment fusion protein; Abatacept; recombinant activated protein C; dornase-alpha DNAse; Enfuvirtide (HIV fusion inhibitor) Anakinra, Botulinum Toxins, e.g., Type A; Samarium [153 m] lexidronam; Perfultren; Cetrorelix; Eptifibatide; Insulin Glargine; Insulin Aspart; Hepatitis B virus small surface antigen (HbsAg); Eptotermin alfa; Protein C; Inactivated hepatitis A virus hepatitis B surface antigen; Dibotermin alfa; IL-2-diptheria toxin fusion protein that targets cells displaying a surface IL-2 receptor; Endostatin; Human insulin-like growth factor binding protein-6.

The therapeutic proteins of the invention can be produced by methods such as those disclosed herein or by other such methods including those disclosed in US patent publication No. 2008/0064862, published Mar. 13, 2008.

The invention encompasses glycosylated fusion protein compositions of matter such as Fc fusion proteins. For example, the invention includes the glycosylated composition of matter for CTLA4-Fc; TNFR-Fc (e.g., TNF receptor type II-IgG, e.g., Enbrel); EPO-Fc (e.g., erythropoietin-Fc); GIRT-Fc (e.g., glucocorticoid induced tumor necrosis factor); cytotoxic IL-2/Fc as well as other Fc fusion proteins.

The invention includes methods for producing multimeric proteins including immunoglobulins, such as antibodies, and antigen binding fragments thereof. Thus, in one embodiment of the present invention, the multimeric protein is an immunoglobulin, wherein the first and second heterologous polypeptides are immunoglobulin heavy and light chains respectively.

In certain embodiments, an immunoglobulin polypeptide encoded by the transcriptional unit of at least one expression vector may be an immunoglobulin heavy chain polypeptide comprising a variable region or a variant thereof, and may further comprise a D region, a J region, a C region, or a combination thereof. An immunoglobulin polypeptide encoded by an expression vector may also be an immunoglobulin light chain polypeptide comprising a variable region or a variant thereof, and may further comprise a J region and a C region. The present invention also contemplates multiple immunoglobulin regions that are derived from the same animal species, or a mixture of species including, but not only, human, mouse, rat, rabbit and chicken. In certain embodiments, the antibodies are human or humanized.

In other embodiments, the immunoglobulin polypeptide encoded by at least one expression vector comprises an immunoglobulin heavy chain variable region, an immunoglobulin light chain variable region, and a linker peptide thereby forming a single-chain antibody capable of selectively binding an antigen.

Some other examples of therapeutic antibodies that may be produced in methods of the invention include, but are not limited, to HERCEPTIN™ (Trastuzumab) (Genentech, CA) which is a humanized anti-HER2 monoclonal antibody for the treatment of patients with metastatic breast cancer; REOPRO™ (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-$\alpha V\beta 3$ integrin antibody (Applied Molecular Evolution/MedImmune); Campath; Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD2O IgG1 antibody (IDEC Pharm/Genentech, Roche/Zettyaku); LYMPHOCIDE™ which is a humanized anti-CD22 IgG antibody (Immunomedics); ICM3 is a humanized anti-ICAM3 antibody (ICOS Pharm); IDEC-114 is a primate anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (CS) antibody (Alexion Pharm); D2E7 is a humanized anti-TNF-$\alpha$ antibody (CATIBASF); CDP870 is a humanized anti-TNF-$\alpha$ Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-$\alpha$ IgG4 antibody (Celltech); LDP-02 is a humanized anti-$\alpha 4\beta 7$ antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); CAT-152, a human anti-TGF-$\beta_2$ antibody (Cambridge Ab Tech); Cetuximab (BMS) is a monoclonal anti-EGF receptor (EGFr) antibody; Bevacizuma (Genentech) is an anti-VEGF human monoclonal antibody; Infliximab (Centocore, JJ) is a chimeric (mouse and human) monoclonal antibody used to treat autoimmune disorders; Gemtuzumab ozogamicin (Wyeth) is a monoclonal antibody used for chemotherapy; and Ranibizumab (Genentech) is a chimeric (mouse and human) monoclonal antibody used to treat macular degeneration.

Proteins produced in transgenic avians in accordance with the invention can be purified from egg white by any useful procedure such as those apparent to a practitioner of ordinary skill in the art of protein purification. For example, the fusion protein molecules (e.g., Fc fusion protein molecules) such as CTLA4-Fc molecules produced in transgenic avians in accordance with the invention can be purified from egg white by methods apparent to practitioners of ordinary skill in the art of protein purification. For example, Fc containing fusion proteins of the invention may be isolated using a Protein A column.

Representative glycosylation structures have been determined for the fusion protein molecules (e.g., Fc fusion protein molecules) such as CTLA4-Fc molecules (CTLA4-Fc) of the invention and are shown in Example 5.

The invention includes the avians (e.g., chicken, turkey and quail) that lay the eggs containing egg white which contains therapeutic protein molecules of the invention comprising one or more of the glycosylation structures disclosed herein.

The following specific examples are intended to illustrate the invention and should not be construed as limiting the scope of the claims.

Example 1

Production of Vector pSIN-OV-3.5-I-CTLA4-Fc-Inv

This vector includes the ovalbumin Dnase hypersensitive sites (DHS) I, II and III, the first exon (exon L), the first intron and the CTLA4-Fc fusion protein coding sequence inserted in frame with the ATG of second exon (exon 1) and with the 3' untranslated region (UTR). The expression cassette is inserted in the inverse orientation into an avian leukosis virus (ALV) vector, which was made self-inactivating (SIN) by deletion of nucleotides 1 to 173 of the ALV LTR sequence.

The vector was constructed as follows: pNLB-3.9-OM-CTLA4-Fc, disclosed in Example 20 of US patent publication No. 2007/0113299, published May 17, 2007, the disclosure of which is incorporated in its entirety herein by reference, was cut with Nae I and Not I. The Not I site was filled in by Klenow reaction. The resulting 8125 bp fragment was gel purified, religated, producing pOM-3.9-CTLA4-dSacI.

pOM-3.9-CTLA4-dSacI was cut with EcoRI and Kpn I and the 8115 bp fragment gel purified. The 3' UTR of the chicken ovalbumin gene was PCRed from BAC 26, disclosed in US patent publication No. 2006/0130170, published Jun. 15, 2006, with the primers 5'-GCGGAATTCAAAGAA-GAAAGCTGAAAAAC-3' (SEQ ID NO: 7) and 5'-GCGGG-TACCTTCAAATACTACAAGTGAAA-3' (SEQ ID NO: 8). The 3' UTR PCR was cut with Eco RI and Kpn I and the 684 bp fragment gel purified. The 8115 bp fragment of pOM-3.9-CTLA4-dSacI was ligated to the 684 bp fragment of 3' UTR PCR, producing pOM-3.9-CTLA4-OV3'UTR.

The 3.5 kb OV promoter region, exon L, first intron and the UTR of exon 1 was PCR amplified with BAC26 as a template and with primers 5'-GGCCTCGAGTCAAGTTCTGAG-TAGGTTTTAGTG-3' (SEQ ID NO: 9) and 5'-GCGCGTCTCTGTCTAGAGCAAACAGCA-GAACAGTGAAAATG-3' (SEQ ID NO: 10). The PCR product was cut with Xho I and Esp3I and the 5094 bp product was gel purified.

A 5' portion of the CTLA4-Fc gene was PCR amplified using pOM-3.9-CTLA4 as a template and primers 5'-GCGCGTCTCAAGACAACTCAGAGTTCAC-CATGGGTGTACTGCTCACACAG-3' (SEQ ID NO: 11) and 5'-GGCCCGGGAGTTTTGTCAGAAGATTTGGG-3' (SEQ ID NO: 12). The PCR product was cut with Esp3I and SacI and the 384 bp product gel purified.

pOM-3.9-CTLA4-OV3'UTR was cut with Sac I and Xho I, the 4473 bp product gel purified and ligated to the 5094 bp OV PCR fragment and 384 bp CTLA4-Fc fragment, producing pOV-3.5-I-CTLA4.

pALV-SIN, disclosed, for example, in Example 10 of US patent publication No. 2007/0124829, published May 31, 2007, the disclosure of which is incorporated in its entirety herein by reference, was cut with Mfe I and Xho I, filled in with Klenow and the 4911 bp fragment gel purified.

pOV-3.5-I-CTLA4 was cut with XhoI and BamHI, filled in with Klenow and the 6957 bp fragment gel purified. This fragment was ligated into the 4911 bp fragment of pAVI-SIN such that the CTLA4-Fc gene and flanking expression elements are in the opposite orientation of the ALV long terminal repeats, producing pSIN-OV-3.5-I-CTLA4-inv which is shown in FIG. 3 and SEQ ID NO: 3.

Example 2

Production of Transgenic Quail Using SIN-OV-3.5-I-CTLA4-inv

Retroviral particles containing the pSIN-OV-3.5-I-CTLA4-inv vector (FIG. 3) and pseudotyped with the VSV envelope protein were produced as described in US patent publication No. 2007/0077650, published Apr. 5, 2007, the disclosure of which is incorporated in its entirety herein by reference. Virus particles were harvested at 48 hours post-transfection, concentrated and on the same day, approximately 4 microliters of the virus suspension containing about $1\times10^5$ particles was injected into the subgerminal cavity of stage X quail eggs. Eggs were sealed and hatched.

Egg whites from chimeric quail were assayed using an ELISA for CTLA4-Fc. The highest expressing quail was found to have CTLA4-Fc in her egg white at approximately 16 μg/ml. The transgenesis level in these quail is estimated at about 5% or less. Thus the level in a G1 should be substantially greater.

Example 3

Construction of pSIN-3.9-OM-CTLA4-Fc

Figure 4:
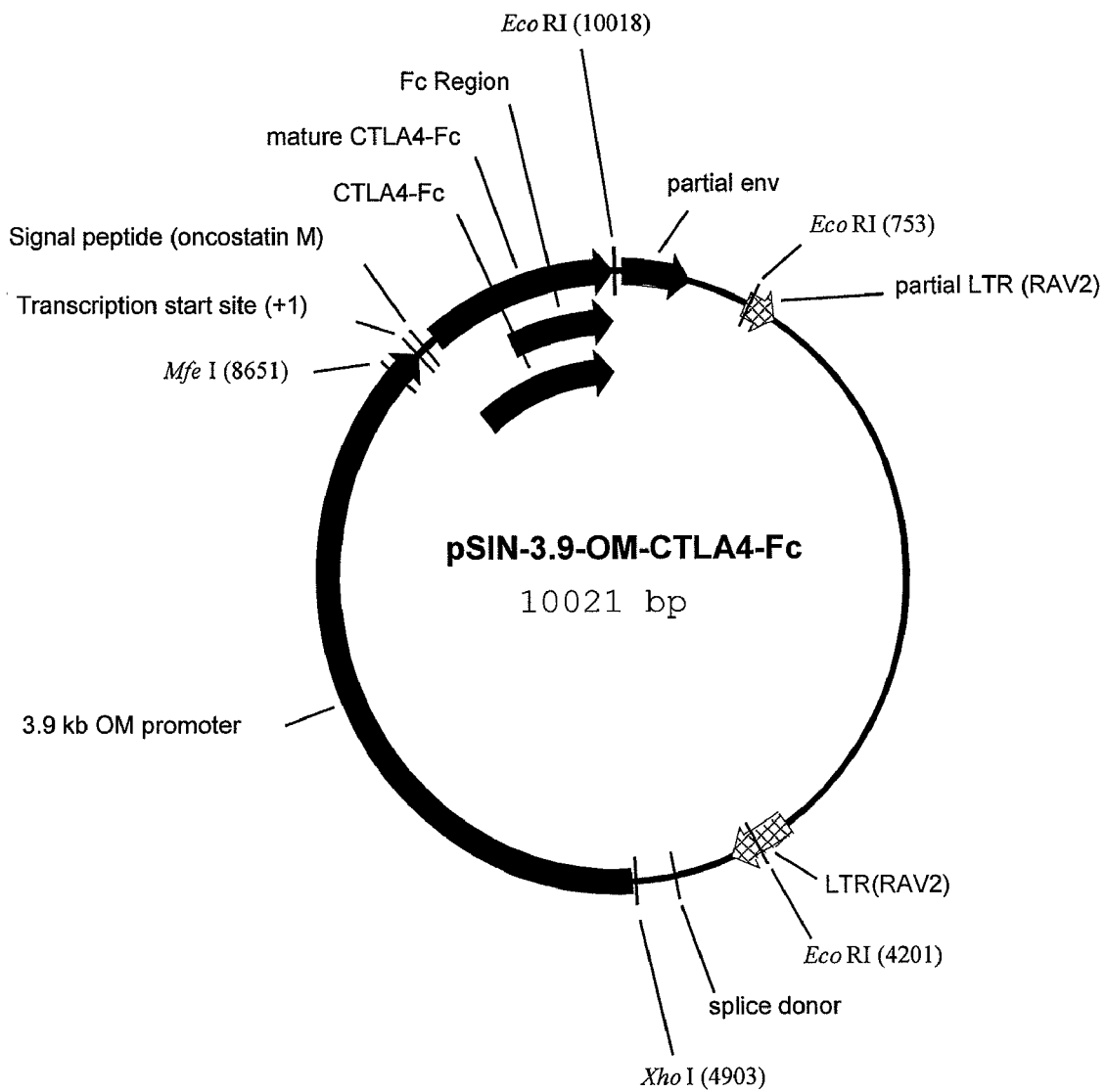
FIG. 4 shows a circular map of the pSIN-3.9-OM-CTLA4-Fc vector. The nucleotide sequence of pSIN-3.9-OM-CTLA4-Fc is shown in SEQ ID NO: 4.

The 4907 bp Mfe I/Xho I fragment of pALV-SIN (disclosed, for example, in US patent publication No. 2007/0124829, published May 31, 2007) was ligated to the 5115 XhoI/EcoRI fragment of pOM-3.9-CTLA4 (shown in FIG. 15 of US patent publication No. 2007/0113299, published May 17, 2007), producing pSIN-3.9-OM-CTLA4-Fc Shown in FIG. 4 and SEQ ID NO: 4, Example 4

Production of Transgenic Chickens Using pSIN-3.9-OM-CTLA4-Fc

Retroviral particles pseudotyped with the VSV envelope protein and containing the pSIN-3.9-OM-CTLA4-Fc (FIG. 4) vector were produced as described in US patent publication No. 2007/0077650, published Apr. 5, 2007. Virus was harvested at 48 hours post-transfection, concentrated and on the same day approximately 7 microliters injected into the subgerminal cavity of stage X eggs. Eggs were resealed and incubated until hatch.

Egg white from hens was assayed using an ELISA for CTLA4-Fc. The highest expressing hen was found to have CTLA4-Fc in her egg white at approximately 0.37 μg/ml. The amino acid sequence of the CTLA4-Fc shown in FIG. 2. The transgenesis level in these hens is estimated at 5% or less.

G-1 hens were obtained by crossing G-0 transgenic roosters to wild type hens and screening for transgenic offspring. Egg white from G1 hens was as high as 440 μg/ml.

Example 5

Carbohydrate Analysis of Transgenic Poultry Derived CTLA4-Fc

CTLA4-Fc was prepared from 25 ml of egg white obtained from eggs laid by G1 transgenic chickens produced as described in Example 4 by first adding 3 volumes (75 ml) of 50 mM NaOAC, pH 4.6 and mixing overnight at 4° C. 10 ml of 0.5 M dibasic sodium phosphate, pH 9.0, was mixed into the egg white/NaOAc solution which was then centrifuged at about 9,000×g for 30 min at 4° C. After centrifugation, the supernatant was filtered through a 0.22 micro filter and then loaded to a 5 ml protein A column which had been equilibrated with about 50 ml of 0.1 M citric acid, pH 3.0 followed by about 20 ml of 1×PBS. The sample was loaded at a 0.5 ml/min flow rate and was then washed with 120 ml of 1×PBS at the same flow rate. The sample was eluted in 1 ml fractions with 0.1 M citric acid, pH 3.0 into collection vessels each containing 60 μl of 1.0 M Tris, pH 9.0.

MALDI-TOF-MS (Matrix assisted laser desorption ionization time-of-flight mass spectrometry) analysis and ESI MS/MS (electrospray ionization tandem mass spectrometry) were performed on the oligosaccharides after release from the peptide backbone of the purified avian derived CTLA4-Fc. Samples of the individual polysaccharide species were also digested with certain enzymes and the digest products were analyzed by HPLC.

N-linked CTLA4-Fc oligosaccharide structures identified were at least one of N-1 and N-2 and at least one of N-3 and N-4 and at least one of N-5 and N-6 and at least one of N-7 and N-8 shown above. Accordingly, the invention specifically includes CTLA4-Fc compositions comprising one or more of N-1, N-2, N-3, N-4, N-5, N-6, N-7 and N-8. The invention also includes CTLA4-Fc compositions comprising at least one of N-1 and N-2 or at least one of N-3 and N-4 or at least one of N-5 and N-6 or at least one of N-7 and N-8 and combinations thereof.

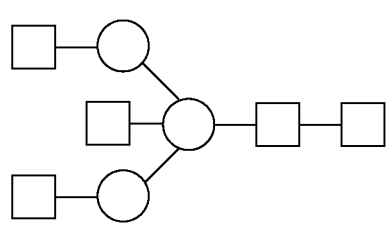

N-1

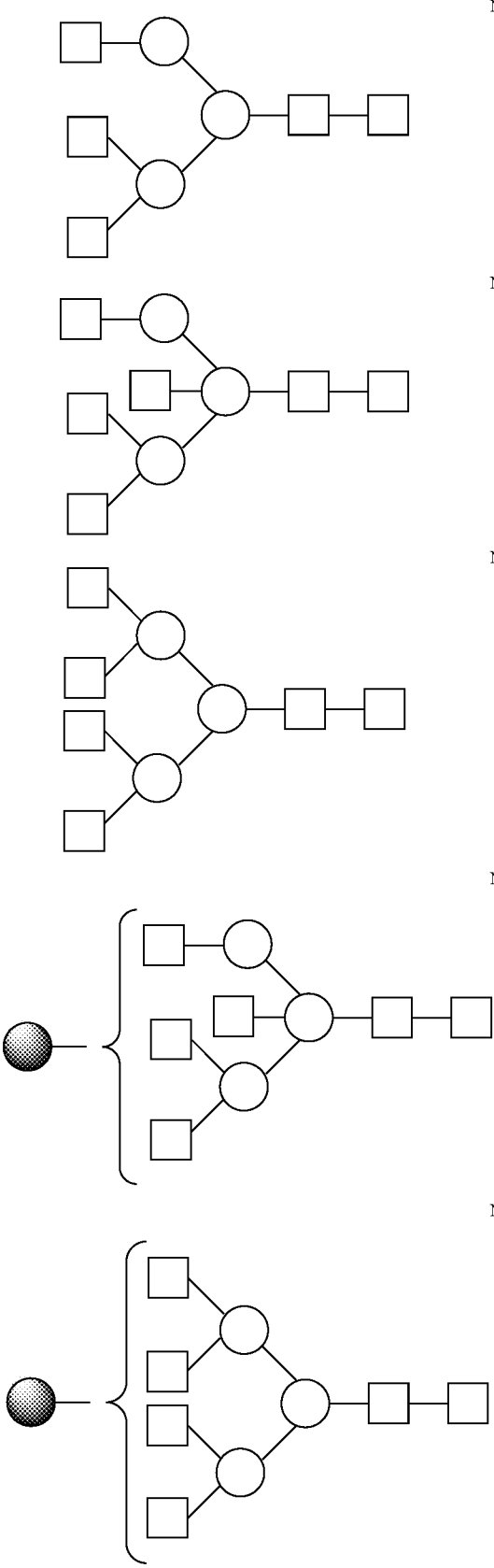

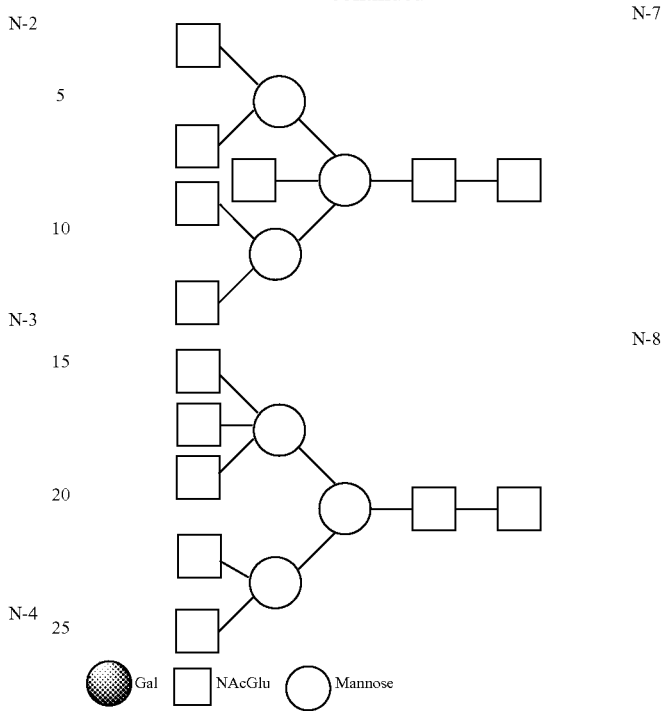

Example 6

Preparation of Avian Derived CTLA4-Fc Conjugated to Linear MPEG-SC-20 KDa

A 5.0 mM stock solution of MPEG-SC-20 KDa is prepared in acetonitrile. A 4.7 µM stock solution of purified CTLA4-Fc isolated from the egg white of a transgenic chicken produced in accordance with the present invention is prepared in conjugation buffer. The conjugation reaction is initiated by mixing 5 ml of the CTLA4-Fc stock with 2.4 ml of conjugation buffer followed by the addition of 400 µl of the MPEG-SC-20 KDa stock solution resulting in a PEG: CTLA4-Fc molar ratio of about 85:1. The reaction is allowed to proceed overnight at room temperature. To stop the reaction, glycine is added to the reaction mix to a concentration of 20 mM, and the mix is allowed to stand for 20 minutes at room temperature. The final volume of the PEG-CTLA4-Fc conjugation mix is about 7.8 ml, containing about 96 µg/ml CTLA4-Fc.

Above is shown MPEG-SC-20 KDa (average molecular weight of 20 KDa) which can be used. The PEG molecule is disclosed in one or more of U.S. Pat. No. 5,122,614, issued Jun. 16, 1992; U.S. Pat. No. 5,612,460, issued Mar. 18, 1997; U.S. Pat. No. 6,602,498, issued Aug. 5, 2003; U.S. Pat. No. 6,774,180, issued Aug. 10, 2004; and US patent publication No. 2006/0286657, published Dec. 21, 2006. The disclosures of each of these four issued patents and one published patent application are incorporated in their entirety herein by reference.

All documents (e.g., U.S. patents, U.S. patent applications, publications) cited in the above specification are incorporated herein by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

---

What is claimed is:

1. A composition comprising isolated human cytotoxic T-lymphocyte-associated antigen 4 (CTLA4)-Fc fusion protein molecules wherein the CTLA4-Fc fusion protein molecules are produced in a transgenic chicken oviduct cell and are isolated from egg white of the transgenic chicken which contains a transgene encoding the CTLA-Fc fusion protein.

2. The composition of claim 1 wherein the oviduct cell is a tubular gland cell.

3. The composition of claim 1 wherein the CTLA4-Fc fusion protein is N-glycosylated.

4. The composition of claim 1 wherein the composition is a pharmaceutical composition.

5. The composition of claim 1 wherein the CTLA4-Fc fusion protein has the amino acid sequence set forth in SEQ ID NO:2.

6. The composition of claim 1 wherein the CTLA4-Fc fusion protein is contained in a hard shell egg.

* * * * *